US012710418B2

(12) United States Patent
Dionne et al.

(10) Patent No.: US 12,710,418 B2
(45) Date of Patent: Aug. 18, 2026

(54) RESONANT NANOPHOTONIC BIOSENSORS

(71) Applicant: The Board of Trustees of the Leland Stanford Junior University, Stanford, CA (US)

(72) Inventors: Jennifer A. Dionne, Menlo Park, CA (US); John Abendroth, Zurich (CH); Mark Lawrence, Saint Louis, MO (US); Jack Hu, Stanford, CA (US); Fareeha Safir, Menlo Park, CA (US); Jefferson Dixon, Staten Island, NY (US); Stefanie S. Jeffrey, Los Altos Hills, CA (US)

(73) Assignee: The Board of Trustees of the Leland Stanford Junior University, Standford (CA)

( * ) Notice: Subject to any disclaimer, the term of this patent is extended or adjusted under 35 U.S.C. 154(b) by 438 days.

(21) Appl. No.: 18/028,873

(22) PCT Filed: Oct. 8, 2021

(86) PCT No.: PCT/US2021/054192
§ 371 (c)(1),
(2) Date: Mar. 28, 2023

(87) PCT Pub. No.: WO2022/076832
PCT Pub. Date: Apr. 14, 2022

(65) Prior Publication Data

US 2023/0341384 A1 Oct. 26, 2023

Related U.S. Application Data

(60) Provisional application No. 63/089,267, filed on Oct. 8, 2020.

(51) Int. Cl.
*G01N 33/543* (2006.01)
*G01N 21/64* (2006.01)
*G01N 21/65* (2006.01)

(52) U.S. Cl.
CPC ..... *G01N 33/54373* (2013.01); *G01N 21/648* (2013.01); *G01N 21/658* (2013.01)

(58) Field of Classification Search
None
See application file for complete search history.

(56) References Cited

U.S. PATENT DOCUMENTS 8,330,952 B2 12/2012 Wu et al.
9,507,064 B2 11/2016 Brongersma et al.
(Continued)

FOREIGN PATENT DOCUMENTS

EP 3591380 A1 1/2020
TW 200718937 A 5/2007

OTHER PUBLICATIONS

Klopfer et al., "Dynamic Focusing with High-Quality-Factor Metalenses", Nano Letters, 20, pp. 5127-5132, published Jun. 4, 2020. (Year: 2020).*
(Continued)

*Primary Examiner* — Rebecca M Giere
(74) *Attorney, Agent, or Firm* — Mueting Raasch Group

(57) ABSTRACT

Optical sensing of biological targets is provided using a metasurface having guided mode resonances with electric field profiles that extend out from the metasurface. Surface functionalization of such metasurfaces can be used to provide sensing for biological targets, such as nucleic acids, proteins, small molecules, extracellular vesicles, and whole cells. Binding of the target to the surface functionalization
(Continued)

can affect the resonance wavelength of the guided mode resonances, thereby providing a sensitive assay for the biological targets.

20 Claims, 19 Drawing Sheets

(56) References Cited

U.S. PATENT DOCUMENTS

| | | | |
|---|---|---|---|
| 9,685,765 | B2 | 6/2017 | Sinclair et al. |
| 9,772,284 | B2 | 9/2017 | Quan |
| 10,393,933 | B2 | 8/2019 | Sinclair et al. |
| 11,391,866 | B2 | 7/2022 | Barton, III et al. |
| 2003/0170613 | A1 | 9/2003 | Straus |
| 2006/0238767 | A1 | 10/2006 | Chen et al. |
| 2010/0126577 | A1 | 5/2010 | Wu et al. |
| 2015/0253525 | A1 | 9/2015 | Hong et al. |
| 2016/0356956 | A1 | 12/2016 | Davoine et al. |
| 2017/0120213 | A1 | 5/2017 | Drmanac et al. |
| 2018/0003706 | A1 | 1/2018 | Trenholm |
| 2018/0003708 | A1 | 1/2018 | Nishizono et al. |
| 2018/0042511 | A1 | 2/2018 | Atanackovic |
| 2018/0241131 | A1 | 8/2018 | Akselrod |
| 2019/0127784 | A1 | 5/2019 | Cunningham et al. |
| 2019/0178805 | A1 | 6/2019 | Su |
| 2020/0241301 | A1 | 7/2020 | Basset |
| 2021/0088819 | A1 | 3/2021 | Dionne |
| 2021/0132255 | A1 | 5/2021 | Barton, III et al. |
| 2022/0011646 | A1 | 1/2022 | Semmlinger et al. |
| 2025/0020596 | A1 | 1/2025 | Hu et al. |

OTHER PUBLICATIONS

USPTO. International Search Report and Written Opinion (PCT ISR) dated Jan. 14, 2022, for parent PCT Application No. PCT/US2021/054192, 8 pages.

Hu et al., "Rapid genetic screening with high quality factor metasurfaces" National Institues of Health, Version 2. ArXiv. Preprint. Oct. 15, 2021 (Oct. 15, 2021) [online] <https://www.ncbi.nlm.nih.gov/pmc/articles/PMC8528080/.

Chen, Wei Ting, et al. "A broadband achromatic metalens for focusing and imaging in the visible." Nature nanotechnology 13.3 (2018): 220-226.

Campione, Salvatore, et al. "Broken symmetry dielectric resonators for high quality factor Fano metasurfaces." Acs Photonics 3.12 (2016): 2362-2367.

Arbabi, Amir, et al. "Dielectric metasurfaces for complete control of phase and polarization with subwavelength spatial resolution and high transmission." Nature nanotechnology 10.11 (2015): 937-943.

Sroor, Hend, et al. "High-purity orbital angular momentum states from a visible metasurface laser." Nature Photonics 14.8 (2020): 498-503.

Aieta, Francesco, et al. "Multiwavelength achromatic metasurfaces by dispersive phase compensation." Science 347.6228 (2015): 1342-1345.

Dionne, Jennifer A., et al. "High Q Metasurfaces for Nonlinear Free-space Optics." Novel Optical Materials and Applications. Optica Publishing Group, 2019. (Abstract only).

The Examiner is respectfully referred to the related, copending foreign patent prosecution of the instant U.S. Appl. No. 18/028,873 family, as follows: European Patent Publication No. 4423807; Chinese Patent Publication No. CN116438137A; and Japanese Patent Application No. 2023-521429.

The Examiner is respectfully referred to patent prosecution of the common Assignee: U.S. Appl. No. 17/089,384, filed Nov. 4, 2020 (which issued as U.S. Pat. No. 11,391,866 B2 as identified above).

The Examiner is respectfully referred to copending patent prosecution of the common Assignee: U.S. Appl. No. 18/712,142, filed May 21, 2024 (published as US-2025-0020596-A1 as identified above), and to its related foreign patent prosecution: Chinese Patent Publication No. CN118613711A; European Patent Publication No. 4437325; and Japanese Patent Application No. 2024-531380.

EPO. Extended European Search Report (EESR) dated Oct. 17, 2024, received for related counterpart European Patent Application No. 21878623.4,8 pgs. Applicant respectfully refers the Examiner to this copending foreign patent prosecution.

Jack Hu, Mark Lawrence, and Jennifer A. Dionne. High Quality Factor Dielectric Metasurfaces for Ultraviolet Circular Dichroism Spectroscopy. ACS Photonics 2020 7(1), 36-42.

JPO. Japanese Office Action dated Jun. 24, 2025, with appended English translation, received for related counterpart Japanese Patent Application No. 2023-521429, 13 pgs. Applicant respectfully refers the Examiner to this copending foreign patent prosecution.

Lawrence M, Barton III Dr, Dixon J, Song JH, van de Groep J, Brongersma ML, Dionne JA. High quality factor phase gradient metasurfaces. Nature Nanotechnology. Nov. 2020; 15(11):956-61. Applicant also submits a second (printable).

CNIPA. Chinese Office Action dated Jan. 29, 2026, with appended English translation, received for related counterpart Chinese Patent Application No. 202180069115.4,14 pgs. Applicant respectfully refers the Examiner to patents cited therein, EP3591380A1 (D1) and US20180003706A1 (D2). These references were previously submitted to the USPTO, and a copy provided if foreign, in Applicant's IDS filed on Nov. 22, 2024 and the IDS filed on Mar. 28, 2023.

* cited by examiner 136 134 136 134 136 134

140

104a 104b 104c 104d 110 138 112 132

130

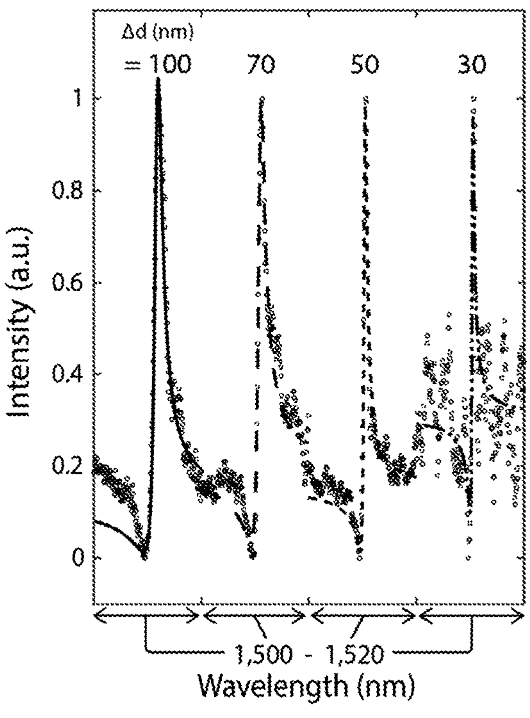
FIG. 3A
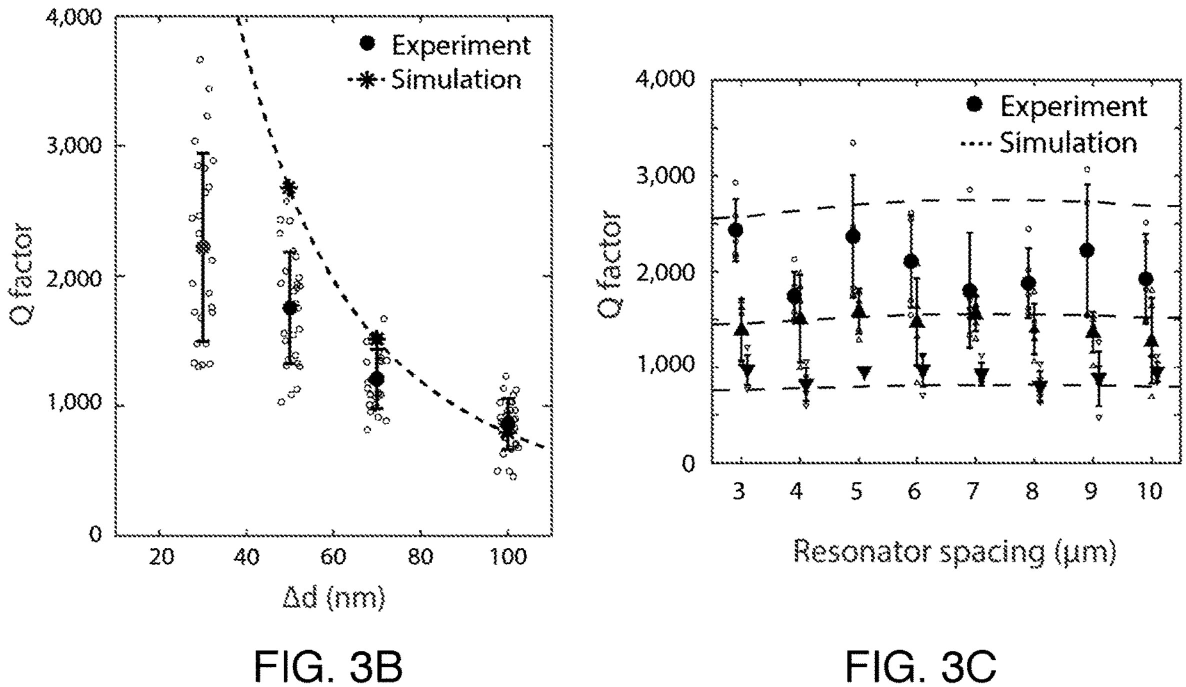
FIG. 3B
FIG. 3C

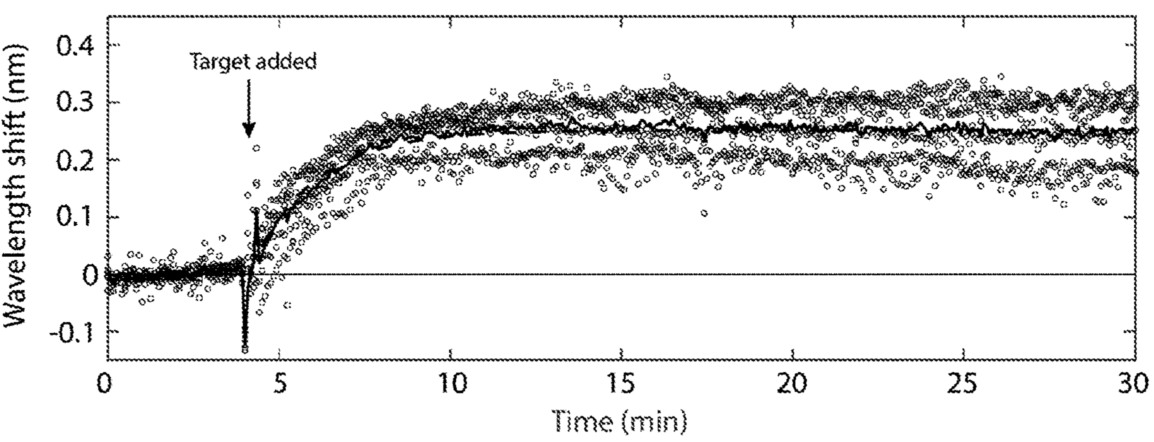
FIG. 5C
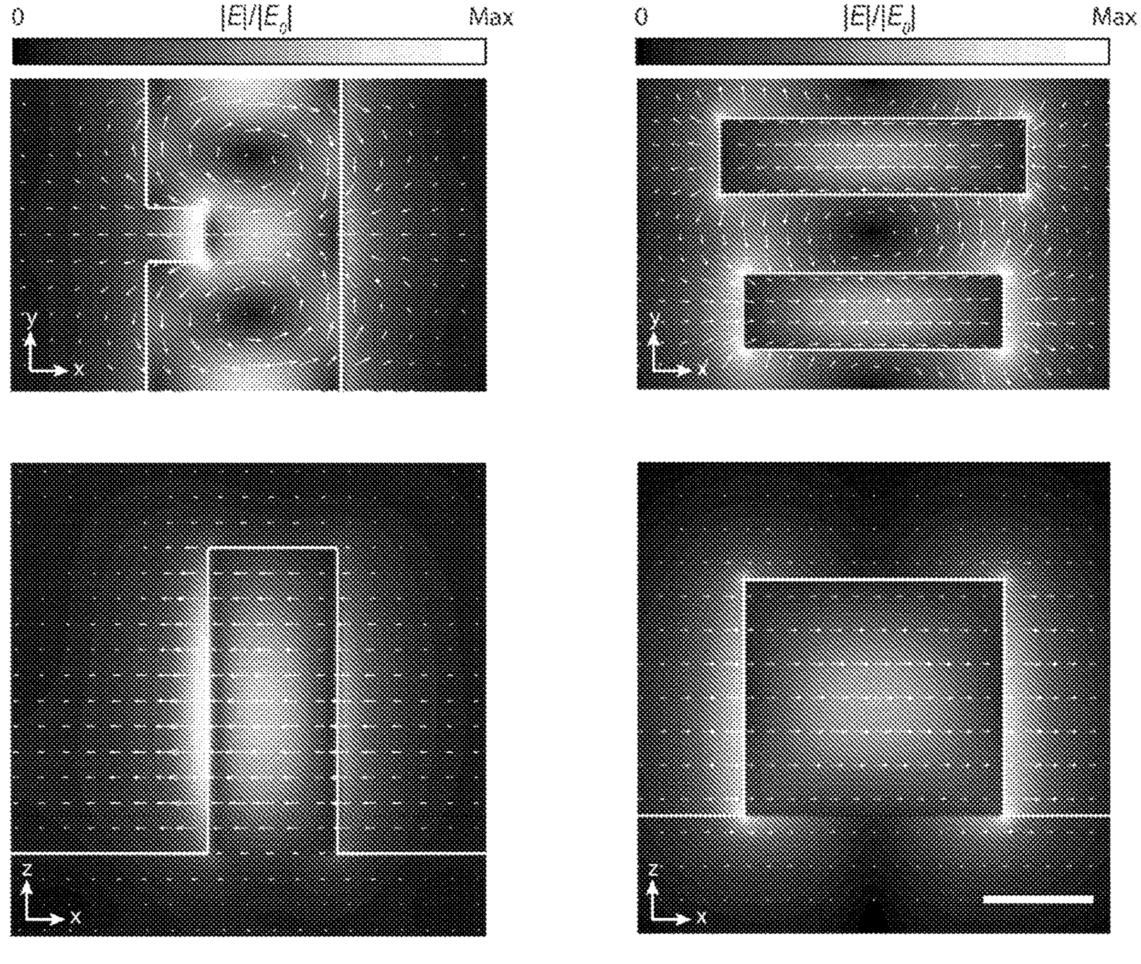
FIG. 6A
FIG. 6B

1006

O
O-Si
O
NH$_2$
HN
O
O-Si
O
HN
O-Si
O
OH
OH
HN
O
OSi
O
N
O
O

FIG. 10B

RESONANT NANOPHOTONIC BIOSENSORS

FIELD OF THE INVENTION

This invention relates to optical biosensors.

BACKGROUND

Nucleic acid, protein, small molecule and whole-pathogen tests are critical for the prediction, detection, monitoring, and treatment of organism and ecosystem health. For example, respiratory panels identify antigen, antibody, nucleic acids, and whole-pathogen signatures indicative of infectious diseases like influenza and Coronavirus; nucleic acids and circulating tumor cells identify cancer and are used to guide treatment; and nucleic acids and small molecules found in environmental samples indicate the health of oceans, freshwater, livestock, soil and air. Most commonly, nucleic acid sequences are identified and profiled using techniques such as reverse-transcriptase polymerase chain reaction (RT-PCR), molecular beacons, and DNA microarrays; likewise, proteins and small molecules are detected using ELISA or lateral flow assays. However, these techniques are either slow and sensitive (e.g., RT-PCR, ELISA) or rapid and imprecise (e.g. lateral flow assays). Novel methods for analyzing biomarkers in patient samples that are rapid and can work at the point-of-care are necessary. Ideally these methods can also comply with the World Health Organization's ASSURED guidelines (Affordable, Sensitive, Specific, User-friendly, Robust and rapid, Equipment-free, Deliverable to those who need them).

SUMMARY

We have developed a new technology that uses optical characterization to rapidly and quantitatively measure: 1) DNA or extracted viral-RNA target binding, 2) antibody binding, 3) whole pathogen (i.e., whole viral or bacterial) binding, and/or 4) small molecule binding to nanofabricated platforms.

We can detect extracted viral-RNA gene sequences from the SARS-CoV-2 genome encoding for different proteins, including envelope proteins, RNA-dependent RNA polymerase, and proteins that form viral nucleocapsids simultaneously and without amplification. We can also detect antibodies, including IgG, IgM, and IgA from serological samples. We can also detect whole-viral or bacterial binding from sputum or saliva. Our technology could also be extended to other viral or bacterial infections beyond COVID-19, to other diseases like cancer, allergens, or neurological disorders, and also to detecting diseases and toxins present in agricultural or environmental settings.

Our platform relies on high-quality-factor ("high-Q") nanostructured dielectric substrates, known as metasurfaces, that generate resonant scattering intensities with high sensitivity that is proportional to adsorbed biomarker load. Metasurfaces are functionalized with receptors, and exposed to patient samples to determine the corresponding viral load from patients tested for viral infection with, e.g., nasopharyngeal, oral/mucal membrane swabs, serological samples, blood, or saliva/breath samples.

The metasurfaces are then illuminated with a laser or light-emitting diode, and the optical readout of the transmitted or reflected incident light provides quantitative, sensitive, and real-time monitoring of nucleic acids, antibody, or whole-pathogen targets without the need for reverse transcription, amplification, or labeling of genes/antibodies of interest. Our rapid and flexible antigen and antibody testing technology is easily deployable, manufacturable, and adaptable to new infectious agents. Our technique promises a limit of detection comparable to current quantitative RT-PCR and ELISA assays, with speed comparable to lateral flow assays.

High-Q Metasurface Design:

We utilize nanostructured Si surfaces, known as metasurfaces, to detect the targeted antigen markers from a patient sample. The metasurfaces are illuminated with a miniature, on-chip laser diode or light emitting diode, and the scattered intensity provides a quantitative measure of fragmented viral-RNA, antibody, or whole pathogen concentration. By relying on free-space resonant metasurfaces, we overcome the typically low signal-to-noise ratio of lateral flow assays and facilitate using off-the-shelf consumer electronics grade camera sensors. Using the nanopatterned Si surfaces over other materials also guarantees the scalability and the cost-effectiveness of this assay; notably, it allows us to capitalize on well-established CMOS fabrication processes with its unique large-scale, low cost manufacturing advantage.

High-quality-factor (high-Q) diffractive optical metasurfaces are considered in U.S. patent application Ser. No. 17/089,384, filed Nov. 4, 2020, and hereby incorporated by reference in its entirety. These metasurfaces include nano-antenna arrays that can be engineered to simultaneously trap and thus amplify light as well as manipulate the way light is scattered to the far-field. The trapping capability, which is key to sensing, is achieved by structuring individual antennas made from transparent, high refractive index materials such as silicon, so that they support guided mode resonances (GMR). Diffraction spectra shows a sharp dip at visible to near-infrared wavelengths, representing a GMR. The lifetime of an optical resonance is characterized by the quality factor (Q), measured by dividing the center frequency by its spectral width. By carefully tuning the geometry, we can ensure that the resonances trap light over thousands of optical cycles, producing an equivalent multiplication of the incident light intensity. In addition to compressing light in time, the metasurface also squeezes light into a very small volume. Taken together these effects result in a substrate whose scattering responds very sensitively to the presence of antigen nucleic acid fragments and antibodies.

High-Q Metasurface Read-Out:

The high quality factor modes within our metasurfaces give a critical signal amplification for sensitive target detection. We can therefore read-out directly scattered (transmitted or reflected) intensities. Importantly, since each nano-antenna is independent from its neighbors, multiplexed detection is possible.

Our metasurfaces can also enable sensitive Raman spectroscopy, for specific detection of whole pathogens. Here, metasurfaces are designed with a high-Q mode at the pump wavelength and a broader-Q mode at the Stokes-shifted wavelengths. Alternatively, a series of high-Q modes can be positioned at the Stokes-shifted wavelengths where features of the pathogen are anticipated.

Finally, our metasurfaces are inherently dispersive. Since our metasurfaces are engineered on the scale of the operational wavelength, ~100-1000 nm, they can efficiently diffract the scattered light. In our previous experiments, we demonstrated that we can systematically tune this diffraction profile independently from the high-Q metasurface resonance. Because of the strong structural dispersion, we can spatially separate the various scattered wavelengths simply by imaging the metasurface with a CCD or CMOS camera. This optical dispersion will reveal high resolution spectral information about the antibodies or pathogens, without the need for bulky, costly optical components such as spectrometers and spectral CCDs.

Metasurface Functionalization for Nucleic Acid/Antigen Testing:

Chemical functionalization of the metasurface platform relies on covalent silanization of metasurfaces with, for example, (3-aminopropyl)trimethoxysilane (APTMS) or 11-aminoundecyltriethoxysilane (AUTES). Amine-to-sulfydryl crosslinking with m-maleimidobenzoyl-N-hydroxysuccinimide (MBS) ester is then used to attach thiolated DNA probes complementary to the gene sequences E, N2, Orflab, and 5'UTR used in current RT-PCR assays. DNA probe concentration and surface densities can be tuned for highest efficiency hybridization with RNA fragments by diluting APTMS self-assembled monolayers with trimethoxy(propyl)silane (PTMS). This well-studied surface functionalization approach via silanization has already been validated by us for reproducible and controllable oligonucleotide attachment.

Metasurface Functionalization for Antibody Testing:

Surface functionalization for antibody assays currently utilize a 6-step process. After mirroring the first two steps of the antigen surface chemistry, we functionalize the surface with a monolayer of a zwitterionic, polyethylene glycol (PEG)-lyated matrix optimized to minimize nonspecific adsorption. This matrix is composed of an optimized ratio of two molecules, 2-{2-[2-(1-mercaptoundec-11-yloxy)-ethoxy]-ethoxy}-ethoxy nitrilotriacetic acid (HS-C11-(EG) 3-NTA) and (2-[2-(2-[11-mercapto-undecyloxy)-ethoxy]-ethoxy)-ethoxy]-ethoxy)-dimethylammonio)acetate, the first of which will eventually bind to our antibody of interest while second increases the density of the monolayer. Subsequent incubation with nickel chloride salt binds to the NTA molecule. This Ni(II)-NTA complex then enabled binding of the RBD region of the SARS-CoV-2 spike protein to our metasurface. The spike protein has been modified with a polyhistidine-tag, increasing the affinity of our spike protein for metal ions, and thereby increasing its bonding affinity with the Ni(II)-NTA complex of our monolayer. Importantly, this functionalization orients the antibody recognition site, allowing for increased likelihood of bonding with our primary antibody.

We position the chip in a sealed holder that allows introduction of liquid patient samples (nasal pharyngeal swabs as well as serological samples) without contamination, and simultaneous optical interrogation and read-out.

Significant advantages are provided. Our assay offers several advantages compared to existing antigen tests: 1) a near-instantaneous read-out (we currently use 30 ms acquisitions); therefore, combined with sample processing (e.g., viral gene fragmentation), our assay can provide antigen results in <15 minutes at the point of care. 2) an extremely low limit of detection, owing to the chips laser-sharp scattering spectra; preliminary experiments indicate a sensitivity of 1000 cp/mL. 3) By relying on nanopatterned Si, we capitalize on the low-cost and scalable fabrication of established high-throughput CMOS fabrication processes. 4) Fluorescent tagging or secondary antibodies are not required; therefore, no reagents are required by users after receiving our product. 5) Massive multiplexing of antigen and antibody testing is possible on a single chip, owing to the "free-space" illumination of the surfaces and our bioprinted functionalization. 6) Our substrates are reusable after washing. 7) Minimal training for use is needed, unlike PCR or ELISA which require a lab technician or health care professional. We project a large user-base of customers in healthcare systems, including doctors/clinics, urgent care facilities, and hospitals; at-home tests could be deployed in the longer-term.

BRIEF DESCRIPTION OF THE DRAWINGS

FIGS. 3A-C show fluid cell characterization of metasurfaces.

FIGS. 5A-C show a biosensing demonstration with SARS-CoV-2 gene fragment targets.

FIGS. 6A-B shows electric field profiles for notched and block waveguide guided mode resonances.

Figure 10B:
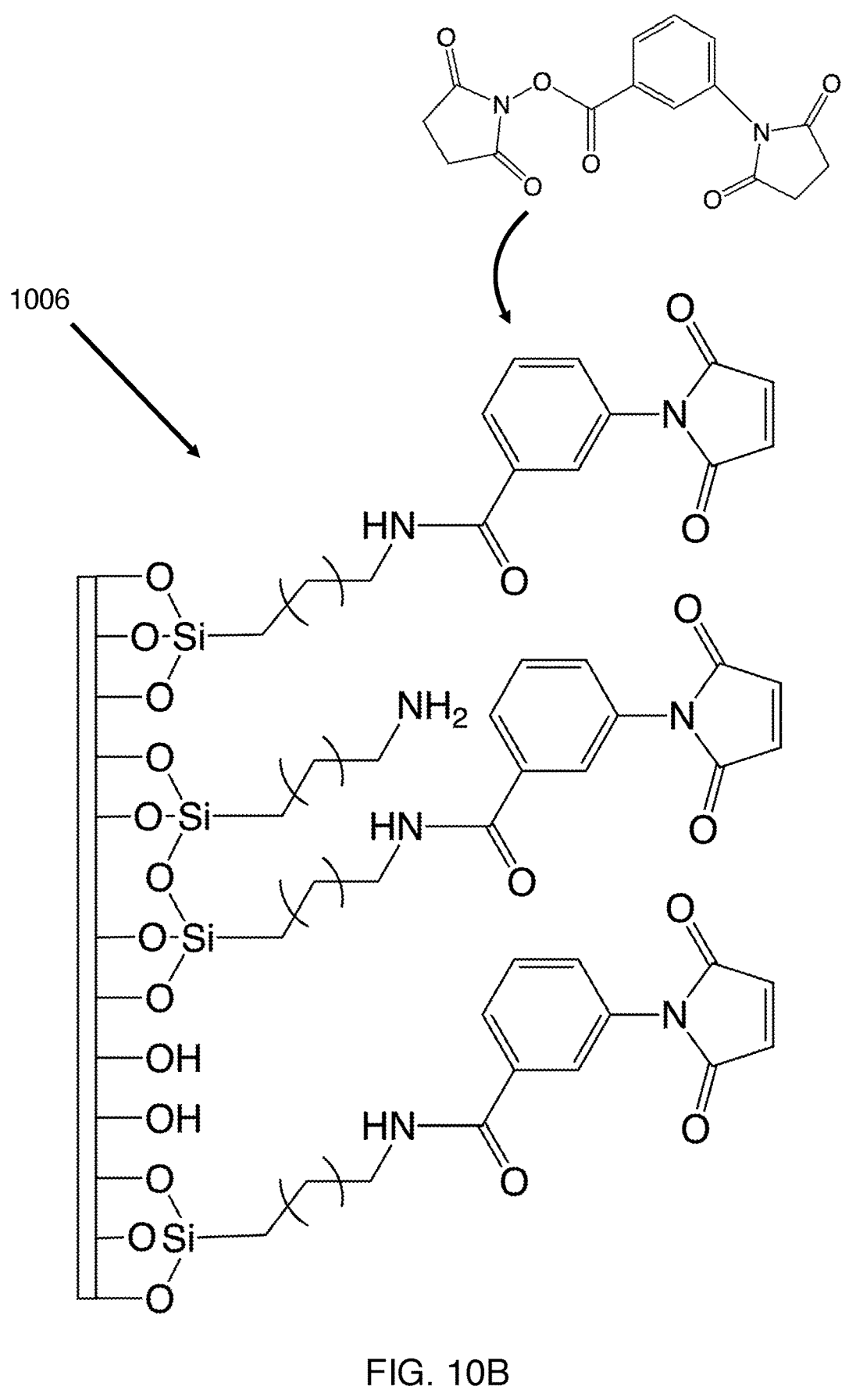

FIGS. 10A-F show an exemplary surface functionalization for protein detection.

DETAILED DESCRIPTION

Section A describes general principles relating to embodiments of the invention. Section B relates to an example of nucleic acid detection. Section C relates to an example of protein detection.

A) General Principles

Figure 1A:
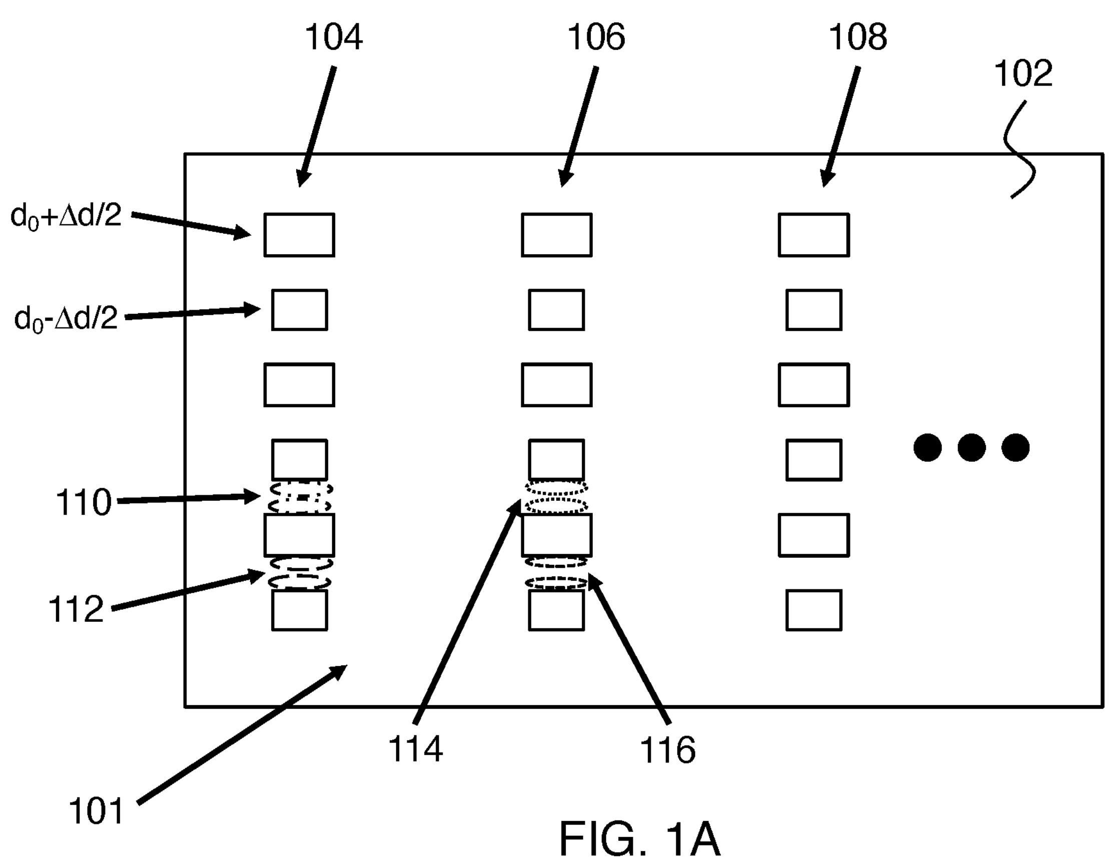
FIGS. 1A-C schematically show several operating principles of embodiments of the invention.
Figure 1B:
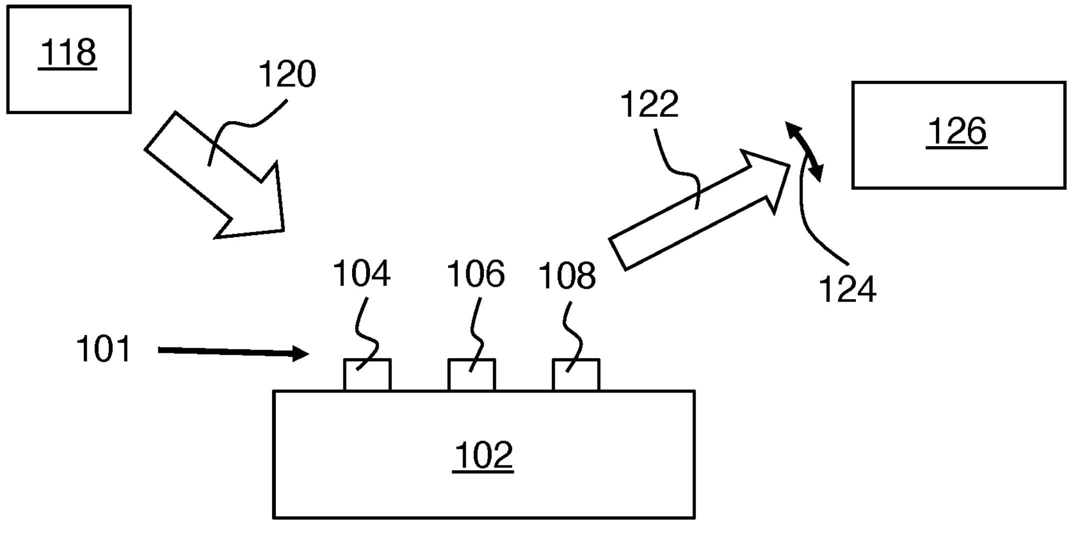
Figures 1C, 2A, 2B:
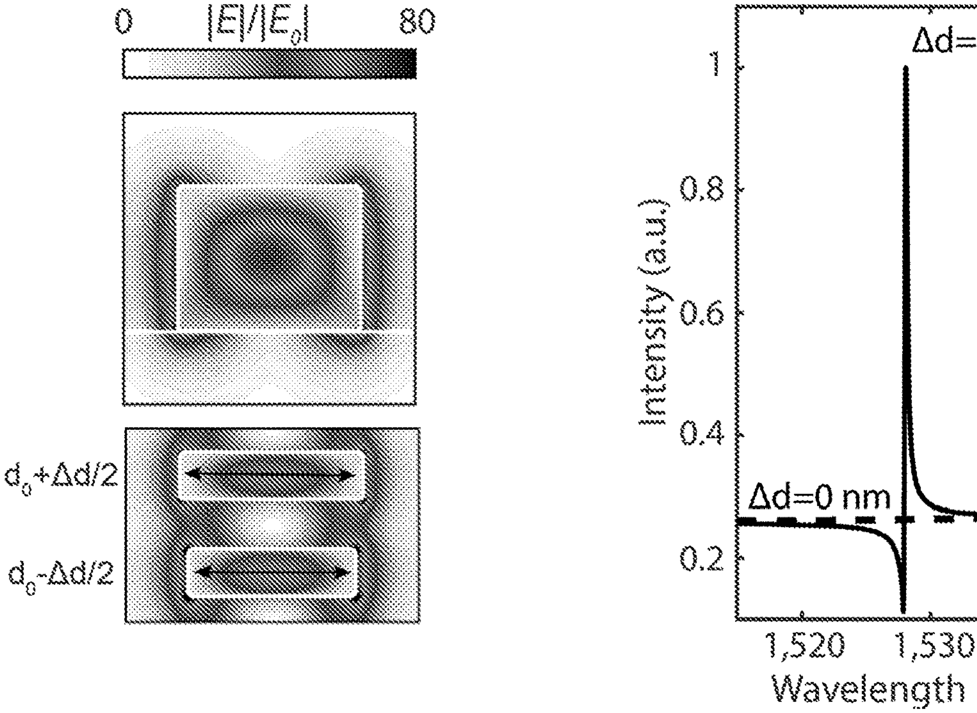
FIGS. 2A-E show design of high-Q sensors.

FIGS. 1A-C schematically show several operating principles of embodiments of the invention. Here FIG. 1A is a top view, FIG. 1B is a side view, and FIG. 1C is an enlarged view. A first exemplary embodiment is apparatus including an electromagnetic metasurface 101 including one or more waveguides 104, 106, 108 etc. disposed on a substrate 102. Three waveguide are shown here, but any number of waveguides (including the special case of a single waveguide) can be employed. Each of the one or more waveguides supports one or more guided modes. Each of the one or more waveguides has a corresponding longitudinal perturbation, whereby at least one guided mode resonance is supported in each of the one or more waveguides. In the example of FIG. 1A, this longitudinal perturbation is the width variation shown on FIG. 1A. Here a longitudinal perturbation of a waveguide is any perturbation that breaks the underlying translational invariance of the waveguide. Such perturbations can be periodic or aperiodic, and can include features such as notches, fins, and length, width and/or height variations of waveguide structures.

Free-space radiation (e.g., radiation 120 from source 118 on FIG. 1B) is coupled to a selected one or more of the guided mode resonances by the longitudinal perturbations of the one or more waveguides. The selected one or more guided mode resonances have electric field distributions that extend outside the electromagnetic metasurface, in order to provide environmental sensing. On FIG. 1A, electric fields extending outside the metasurface are schematically shown as 110, 112, 114, 116, with the different line patterns schematically indicating different surface functionalization of these parts of the metasurface, as further described below.

In cases like FIG. 1A where the waveguides include periodic longitudinal gaps, it is expected that such high field regions are present in all the gaps, but for simplicity in FIG. 1A only a few of these are shown. Preferably, the selected one or more guided mode resonances have a free-space fraction of electric field energy of 0.2 or more (see section B7.1).

The apparatus can further include an optical source 118 configured to provide the free-space radiation 120 (FIG. 1B). The apparatus can further include an optical detector 126 configured to receive output radiation 122 from the electromagnetic metasurface. The output radiation can be reflected radiation, transmitted radiation, scattered radiation, diffracted radiation, and/or Raman-scattered radiation.

The detector 126 can be configured to determine a spectrum of the output radiation 122 based on dispersion 124 caused by the one or more waveguides. Note that in the side view of FIG. 1B, waveguides 104, 106, 108 etc. can act as a diffraction grating, which is one example of how such dispersion can be provided.

The apparatus can further include a surface functionalization disposed on the electromagnetic metasurface and configured to selectively bind one or more analytes in proximity to the electromagnetic metasurface. FIG. 1C is an enlarged view of waveguide 104 of FIGS. 1A-B (rotated a quarter turn), where waveguide blocks 104*a* and 104*b* have surface functionalization 130 on them, and where waveguide blocks 104*c* and 104*d* have surface functionalization 132 on them. For ease of illustration the surface functionalization is only shown on one surface of the waveguide blocks, but in practice it would typically be present on all surfaces of the waveguide blocks.

Preferably, as in the example of FIG. 1C (and also as shown more schematically on FIG. 1A), different parts of the metasurface have different surface functionalization. This allows different parts of the metasurface to respond selectively to different targets. For example, on FIG. 1C, functionalization 130 is a match for target 134 as shown by bound target 138. Similarly, functionalization 132 is a match for target 136, as shown by bound target 140.

This can be regarded as configuring the electromagnetic metasurface as an array of one or more sensor pixels, each sensor pixel including a corresponding part or all of one of the one or more waveguides. Such an array of one or more sensor pixels can be 1-D or 2-D. Per-pixel selective surface functionalization can be used to provide multiplexed sensing of two or more distinct analytes.

Practice of the invention does not depend critically on the kind of analyte being detected. Suitable analytes include but are not limited to: nucleic acids, proteins, small molecules, extracellular vesicles, and whole cells.

Preferably a detection sensitivity of the one or more analytes is 10 fM or better, to enable detection of the one or more analytes without a prior analyte amplification step. Here the detection sensitivity for an analyte is the minimum detectable concentration of that analyte. This opens up the important possibility of being able to avoid expensive and time-consuming analyte amplification processes, such as PCR. Another important advantage of the current approach is high dynamic range. Preferably the dynamic range for detection of the one or more analytes is 10 dB or more

B) Example 1—Nucleic acid Detection

B1) INTRODUCTION

Genetic screening methods have enabled significant advances in the prediction, detection, treatment, and monitoring of organism and ecosystem health. For example, respiratory panels identify pathogen nucleic acids indicative of infectious diseases like influenza and Coronavirus disease 2019 (COVID-19); tissue and liquid biopsies detect cancerous genetic mutations, likelihood of recurrence, and are used to guide treatment; and emerging environmental DNA sensors monitor the health of oceans, freshwater, livestock, soil and air. Current genetic screening methods include polymerase chain reaction (PCR), next-generation sequencing (NGS), Sanger sequencing, and DNA microarrays. Each utilizes oligonucleotide amplification followed by optical tagging to sensitively detect target sequences. Despite their tremendous utility in laboratory settings, translation of these screening methods to clinical and point-of-care applications is ultimately limited by their reliance on “traditional” optical signal transduction (absorption and fluorescence). Even with the best optical tags, sensitive and specific readouts are generally only achieved with time consuming thermal cycling and/or costly reagents for nucleic acid amplification.

Rather than amplifying the concentration of the biomolecule, we postulated that light could be resonantly amplified to help enable compact, point-of-care biomarker screening methods. Photonic devices strongly confine and scatter light; when decorated with molecular probes, target analyte binding alters the optical signal due to subtle changes in the polarizability or refractive index of the resonator environment. Plasmonic sensors are among the most common affinity-based biosensors, but have larger limits of detection set by the metals' intrinsic absorption; the resulting low quality factor (Q) resonances (Q~10) give rise to poor differentiation of small binding signals (where a resonator's sensing figure of merit (FOM): Sensitivity (resonant wavelength shift per refractive index unit (RIU) change) divided by the full width at half maximum (FWHM) of the mode is ca. 1-10 $RIU^{-1}$). More recently, dielectric nanoantennas and metasurface based sensors have been designed with Q factors of 10's-100's, with similar improvements in the FOM. Unlike high Q whispering gallery mode resonators and photonic crystal microcavity devices, these metasurfaces can be illuminated from free space and far field scattering can be readily controlled, an advantage in scalability and integration of sensors in imaging based devices. However, these systems typically rely on delocalized resonant modes formed from extended two-dimensional arrays; the resultant large modal volumes reduce responses to binding of small amounts of target molecules. Additionally the larger footprint of extended arrays limits the dense incorporation of sensing elements for multiplexed analyte detection and data driven analyses.

In this work, we report a new genetic analysis platform based on our lab's development of high quality factor metasurfaces. These metasurfaces include subwavelength nanoantennas that strongly confine light in the near field while affording precise control over far-field scattering. We design resonators that exhibit average Q's in buffered biological media of 2,200, with strong field penetration into the surrounding environment for sensitive biomarker detection. We show that the FOM of our sensors is 400 $RIU^{-1}$, in good agreement with our computational model and significantly larger than existing nanophotonic sensors. We functionalize our resonators with self-assembled monolayers of DNA probes complementary to the SARS-CoV-2 E and ORFlab gene sequences. Hybridization of target nucleic acid fragments to the surface probes results in a rapid (<5 minute) change in the resonant wavelength, with sensitivities and specificities up to 94% and 96%, respectively. Due to the spatially localized nature of the high Q resonances, individual sensing pixels can be patterned at densities of 160,000+ features per square cm, promising analyte parallelizability across a multitude of biomarkers.

B2) INDIVIDUALLY ADDRESSABLE HIGH-Q RESONATOR SENSING PLATFORM

FIG. 1A is a top view of the metasurface geometry of this example. Here silicon waveguides 104, 106, 108 etc. are disposed on a substrate 102. The longitudinal perturbation of this example is a width perturbation Δd. Geometrical parameters of the resonators are height (h)=500 nm, $d_0$=600 nm, thickness (t)=160 nm, block spacing ($a_y$=330 nm), interchain spacing ($a_x$=10 μm), and Δd varied between 30-100 nm.

Figure 2C:
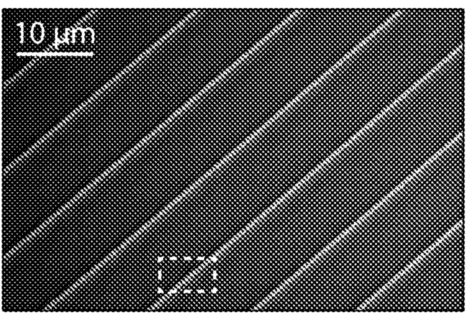
Figure 2C:
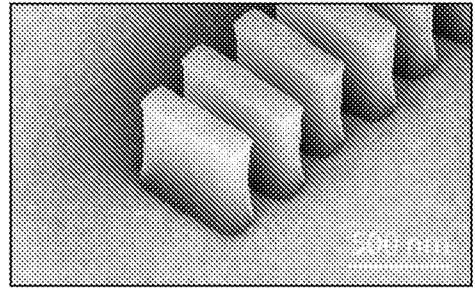
Figure 2D:
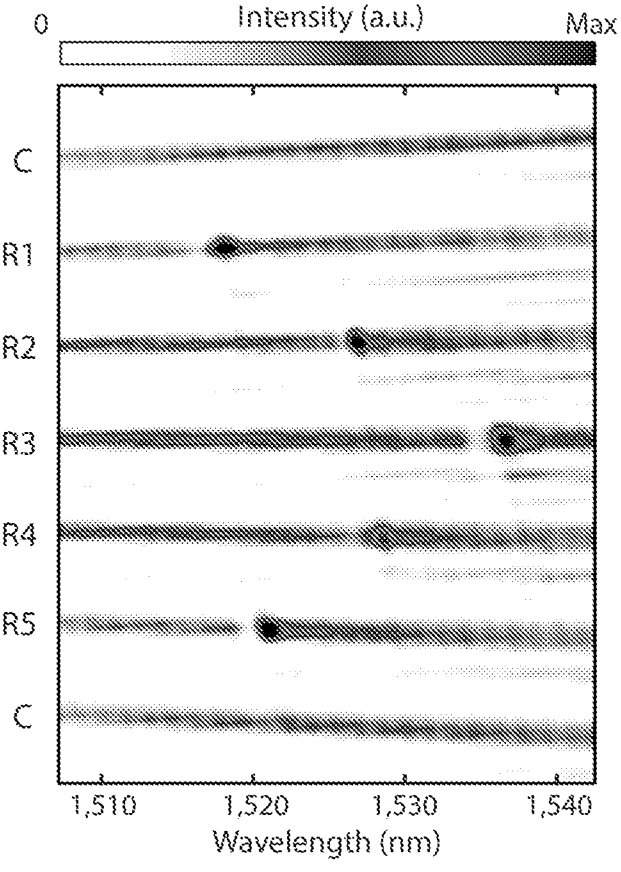
Figure 2E:
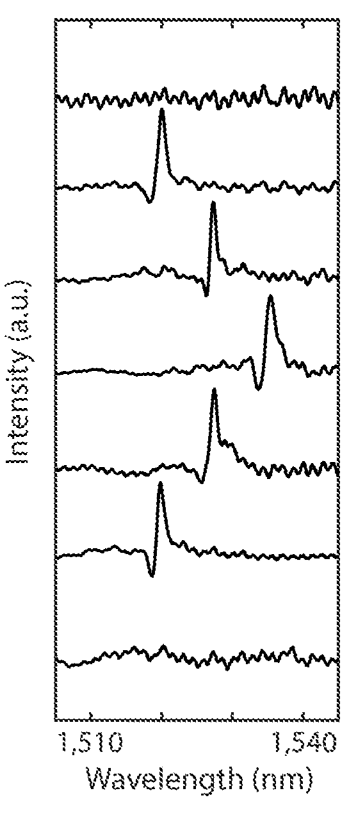

FIG. 2A shows simulated electric near-field enhancements for a resonator with Δd=50 nm. FIG. 2B shows simulated cross-polarized transmission response of metasurface illuminated with normally incident linearly polarized plane waves. Responses are normalized to intensity maximum of perturbed resonator. FIG. 2C shows SEM micrographs of metasurface device composed of multiple individually monitored and tuned resonators, where the bottom image is an enlarged view of the indicated section of the top image. FIG. 2D shows a spectral image from an array with 7 resonators where C denotes nanostructures with no perturbation Δd=0 nm and R1-R5 having perturbation Δd=50 nm. Resonance positions are modulated by adjusting block length where $d_0$=595 nm for R1 & R5, $d_0$=600 nm for R2 & R4, and $d_0$=605 nm for R3. FIG. 2E shows Row averaged transmitted intensities corresponding to FIG. 2D.

This sensor design includes columns (or rows) of Si nanoblocks illuminated with near-infrared light. Each column constitutes a one-dimensional guided-mode resonant (GMR) metasurface; the periodic modulation of block widths within each row, characterized by Δd, allows for finite, but suppressed dipolar radiation and free space coupling to otherwise bound waveguide modes. The resulting long resonant lifetime translates to strong electric near-field enhancements (FIG. 2A). Notably, electric fields at the surface of Si blocks are enhanced by 80×. Due to the gaps between discrete silicon blocks within the resonator, 29% of the electric field energy is exposed to the surrounding medium compared with 8% in a continuous or partially notched waveguide (see also section B7.1 and FIGS. 6A-B). This field concentration in the gaps leads to greater sensitivity to surface-bound analytes. Additionally, these Si resonators exhibit sharp scattering responses in the far-field. As seen in FIG. 2B, calculated transmission spectra Q-factors exceed 5,000 for Δd=50 nm, and can be further increased with decreased d (vide infra).

We fabricate Si resonators atop a sapphire substrate (FIG. 2C) (see section B8). Utilizing a near-infrared supercontinuum laser and spectrometer equipped transmission microscope, we illuminate the metasurfaces at normal incidence and simultaneously measure the transmitted spectra from multiple resonators (FIG. 2D). By modulating the block lengths in adjacent nanostructures by ±5 nm, we intentionally vary the spectral position of the resonant mode, highlighting that each waveguide structure can be individually addressed and tuned as a distinct resonator (FIGS. 2D-E); in other words, our high-Q resonances do not rely on interchain coupling or an extended 2D array effect. This spatial localization of the optical modes makes our platform ideally suited for the integration of densely distributed and multiplexed sensor arrays.

B3) GUIDED-MODE RESONANT METASURFACE CHARACTERIZATION

FIGS. 3A-C show fluid cell characterization of metasurfaces. FIG. 3A shows spectra from resonators with varying Δd. The solid lines represent fits to a Lorentzian oscillator. FIG. 3B show quality factor of resonances with different Δd. Bold markers and error bars are the mean and standard deviation for N=30 resonators at each condition. Stars represent simulated values and the dashed line is a fit to predicted values from coupled mode theory (section B7.2). FIG. 3C shows quality factor as a function of resonator spacing where the mean and standard deviation are for N=5 resonators at each condition.

Our metasurfaces are sealed in a 3-D printed fluid cell and characterized in phosphate-buffered saline (PBS) solution (1× concentration) to represent physiological conditions for biomolecule detection. In FIG. 3A, we vary the perturbation Δd along the block chain from Δd=100 nm to Δd=30 nm and observe a decrease in the resonant linewidth for 25-30 individual resonators at each condition. Importantly, in our high-Q metasurface design, the coupling strength between free space radiation and the GMR is dictated by the degree of asymmetry along the waveguide. Since silicon is lossless in the near infrared, radiative loss dominates the GMR resonant lifetime and Q factor. Thus, shrinking Δd we observe scattering responses with average Q factors of 800 (at Δd=100 nm) increasing to 2,200 at Δd=30 nm and even observing Q's above 3,000 for individual resonators (FIG. 3A). These Q factors represent a two-three order of magnitude increase compared to reported plasmonic biosensors, and a significant (>5×) increase compared to other metasurface biosensors, yielding a FOM of ~400. Our experimental values are likely limited due to scattering losses caused by fabrication imperfections. We also note that water has non-negligible absorption in the 1,500 nm wavelength range that may limit our attainable experimental Q factors (section B7.2 and FIG. 7). Designing future metasurface resonances in an optical transparency window of biological media (such as 1,300 nm) and optimizing fabrication processes may further improve performance, with Q factors in the millions potentially attainable; future iterations of our metasurface could offer the single particle sensitivity of high-Q microcavities, but with the ease of integration and compactness afforded by free-space coupling.

Due to the localization of the mode along each individual row, resonators can be spaced laterally at least as close as 3 μm without affecting the GMR (FIG. 3C). Based on our fabricated waveguide length of 200 μm, our devices feature sensor arrays with densities of over 160,000 sensors per $cm^2$. Due to the slow group velocities of the GMR's, losses due to finite size effects can be suppressed, and 50 μm waveguides can be fabricated with comparable Q (FIGS. 8A-D), yielding feature densities over 600,000 sensors per $cm^2$. These large sensor densities offer an avenue for robust statistical analysis in diagnostic studies as well as a platform for multiplexed detection of many distinct biomarkers in parallel.

B4) SELF-ASSEMBLED MONOLAYER FUNCTIONALIZATION AND SENSING

Figure 4A:
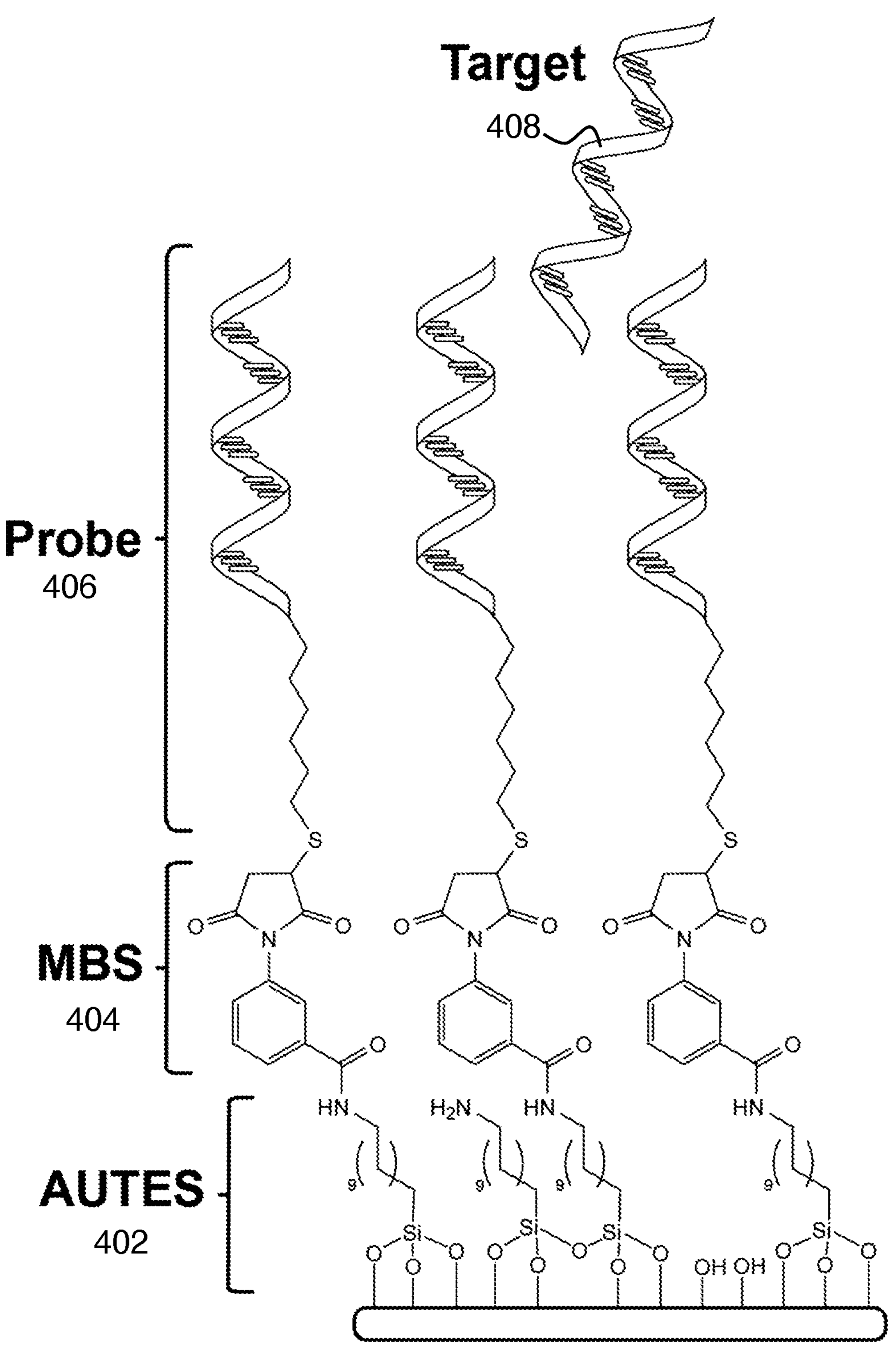
FIGS. 4A-D show DNA monolayer functionalization and resonant wavelength shift measurement.
Figure 4B:
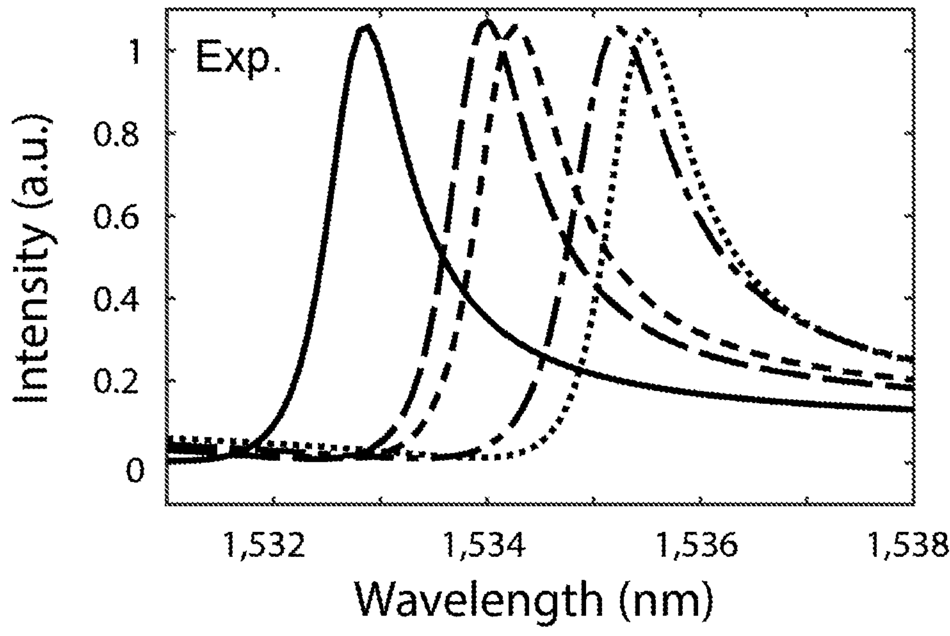
Figure 4C:
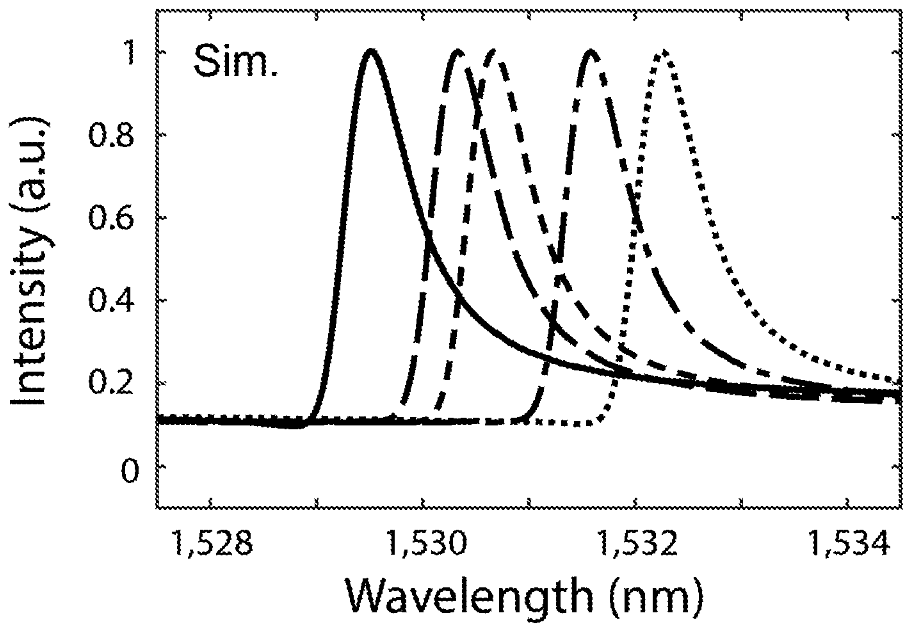
Figure 4D:
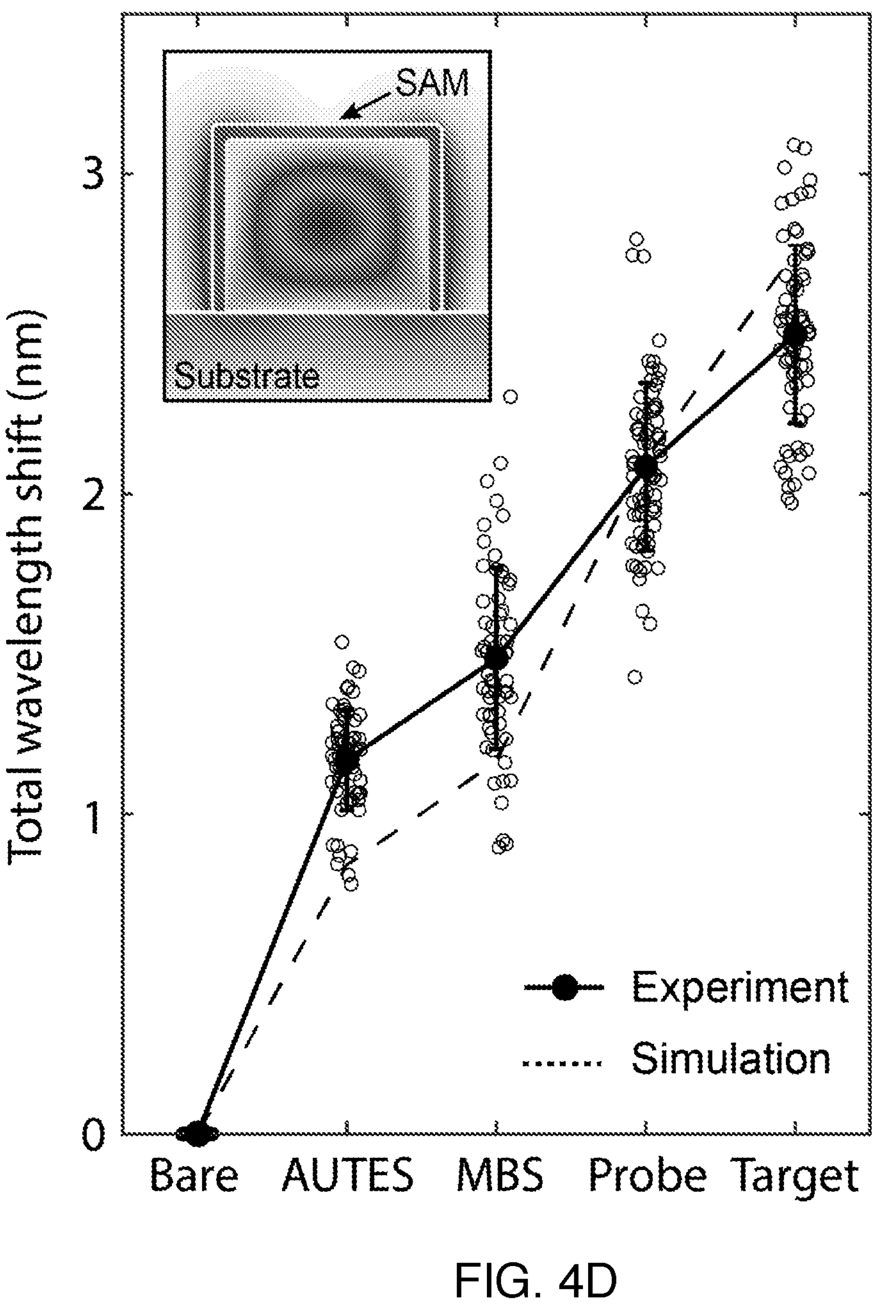

FIGS. 4A-D show DNA monolayer functionalization and resonant wavelength shift measurement. FIG. 4A is a schematic of chemical components utilized in immobilizing DNA self-assembled monolayers (SAM) onto the silicon nanostructures. Target DNA fragments for this study are portions of the E and ORF1 genes from the SARSCoV-2 virus. FIGS. 4B and 4C show experimentally measured and simulated, respectively, resonance wavelength shift responses with the addition of each molecular layer in the SAM, including complementary nCoV.E target binding. The solid lines show fits to a Lorentzian oscillator. The difference in absolute wavelength values between experimental and simulated spectra can be attributed to slight dimension variations in the fabricated structures. FIG. 4D shows total resonant wavelength shift during SAM functionalization and DNA sensing as referenced from initial measurements on bare silicon structures. Markers represent individual measurements from N=75 independent resonator devices and bolded markers and error bars are the mean and standard deviation of the measurements.

To utilize our sensor arrays for gene detection, we modified the silicon surface with DNA monolayers, where complementary nucleic acid sequences serve as capture molecules for a specified target. Self-assembled monolayers (SAMs) are deposited in a three-step process to covalently link 26 base pair single-stranded (ssDNA) DNA probes over the entire metasurface chip surface. The silicon surface is first functionalized with an amine-terminated silane (11-aminoundecyltriethoxysilane, AUTES), and then cross-linked via a heterobifunctional molecule (3-maleimidobenzoic acid Nhydroxysuccinimide ester, MBS) to thiolated ssDNA probes (section B8). In this study, we considered nucleic acid fragment targets of the envelope (E) and open reading frame 1b (ORF1b) genes of the SARS-CoV-2 virus (GenBank accession: MT123293.2 positions 26326→26351 and 18843→18866, respectively) (FIG. 4A). On FIG. 4A, the AUTES, MBS and probe layers of the surface functionalization are references as 402, 404, and 406, respectively. The target is referenced as 408.

As a proof of principle, we use synthetic DNA targets, but note that viral RNA will analogously hybridize to complementary DNA probes. In FIG. 4B, measured spectra show clear resonant wavelength shifts as consecutive molecular monolayers of AUTES, MBS, and the probe DNA are grafted to the resonator surface. Monolayers were modeled as thin dielectric shells surrounding the silicon blocks and simulated responses show close agreement with the experimental resonance shifts (FIG. 4C). Upon adding the target SARS-CoV-2 gene, a clear, 0.4 nm resonant shift is observed (FIG. 4D). Data was collected from N=75 resonators, and we note that the high density of sensing elements on our chips can enable significant increases in measurement throughput compared to typical photonic sensors where signals are averaged over larger 2-D arrays. The deviation between experimental and simulated wavelength shifts for the AUTES and MBS layers is likely due to the tendency for aminosilane molecules to form multilayer structures; differences in the attachment of DNA probes and subsequent target hybridization are likely due to a strong influence of steric hindrance and electrostatic repulsion effects on the packing density and hybridization efficiency of the DNA strands.

B5) RAPID AND SPECIFIC GENE FRAGMENT DETECTION

Figure 5A:
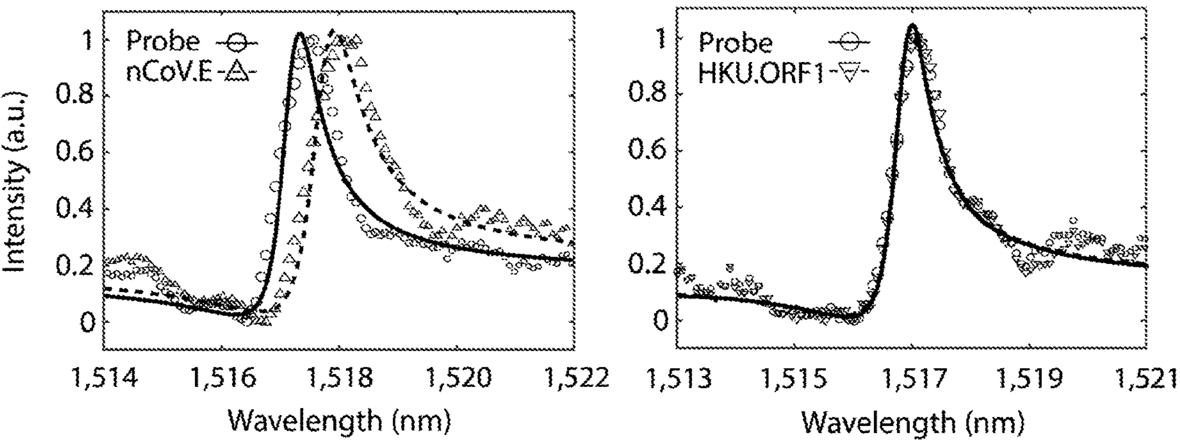
Figure 5B:
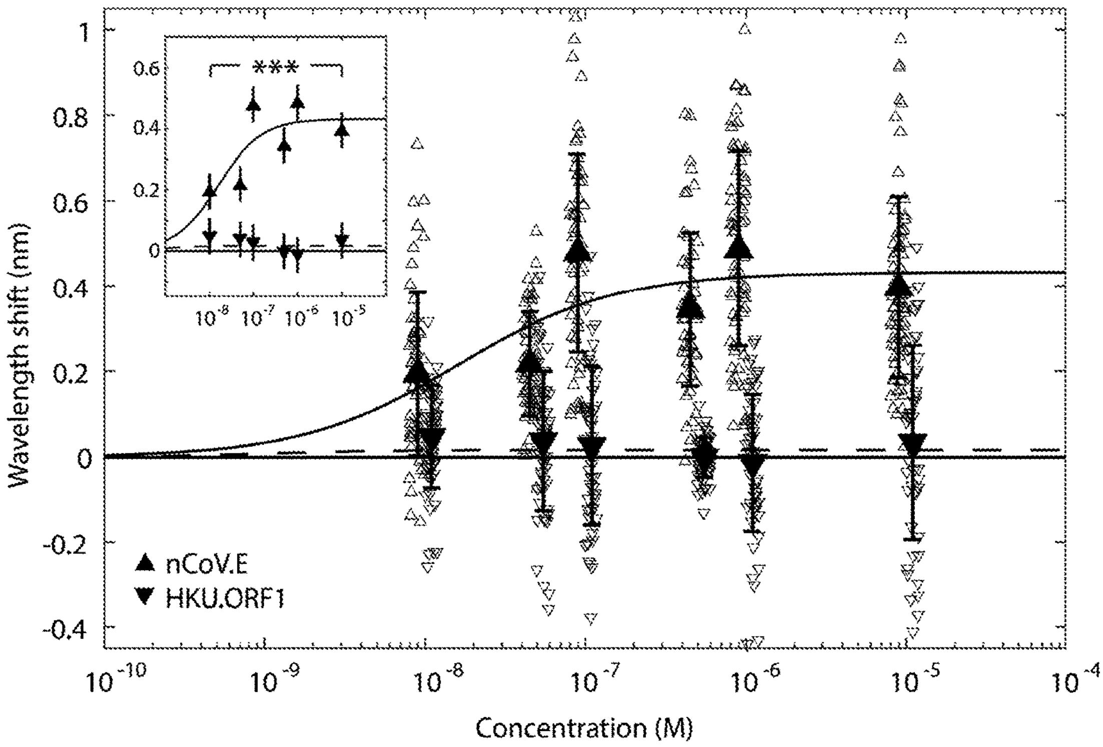

FIGS. 5A-C show a biosensing demonstration with SARS-CoV-2 gene fragment targets. FIG. 5A shows measured spectra that indicate significant wavelength shifts with complementary DNA binding (left) and minimal signal changes when introduced to non-complementary sequences (right). FIG. 5B shows concentration dependent binding responses for both nCoV.E and HKU.ORF1 targets incubated on metasurface devices functionalized with only nCoV.E complementary probes. Error bars indicate standard deviations of measurements from N=50-75 measurements from distinct resonators for each target and concentration condition. Dashed lines show fits to the Hill equation. The inset of FIG. 5B shows that one-way ANOVA and post-hoc Tukey's HSD tests confirm statistically significant differences in binding responses for nCoV.E and HKU.ORF1 targets. Markers represent mean values and bars represent 99% confidence intervals. *P<0.002 vs. non-complementary targets. FIG. 5**C shows kinetic binding responses for 6 resonators incubated with 100 nM of nCoV.E targets. The solid line is the mean of experimental measurements.

Figures 9A, 9B:
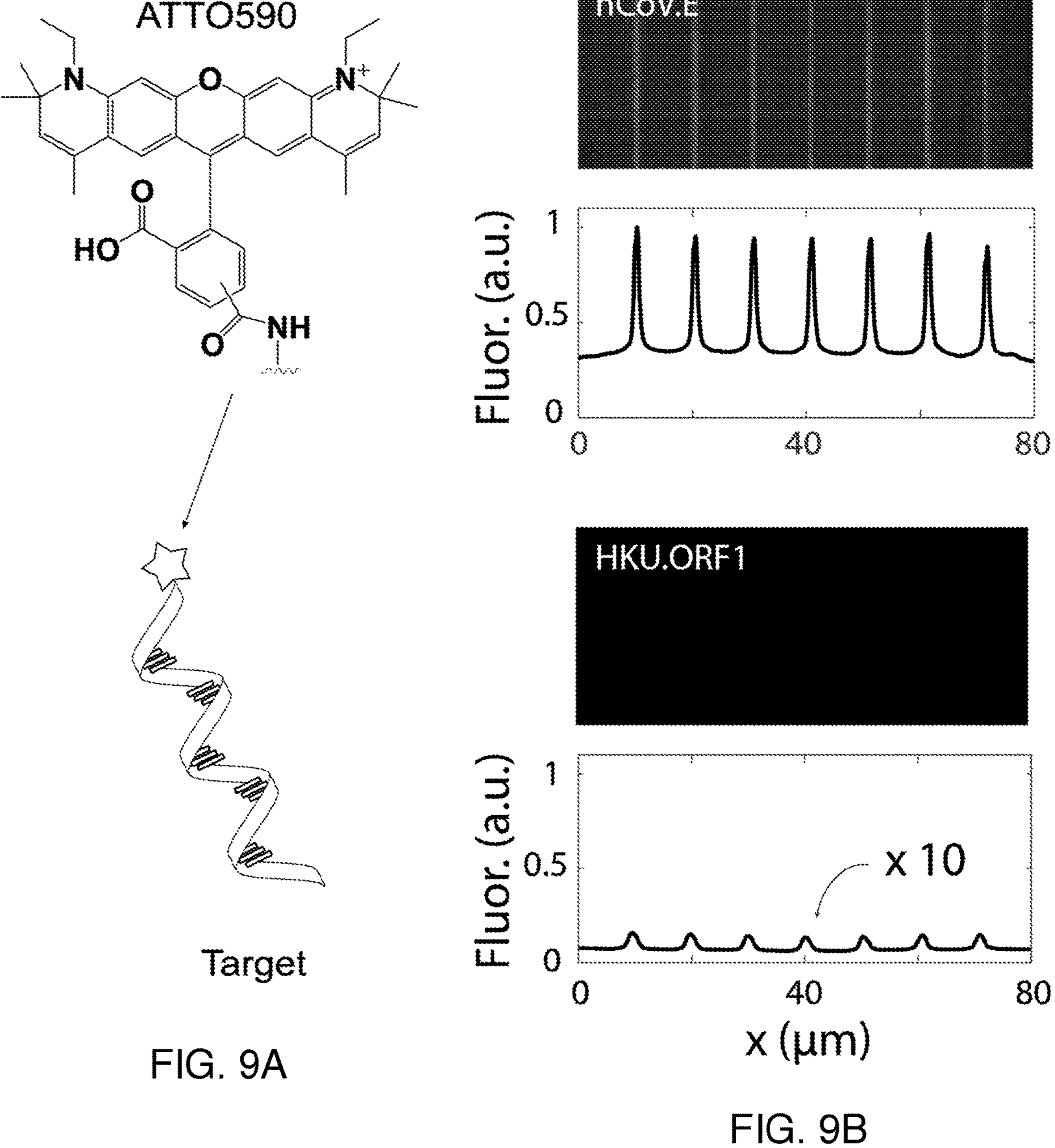
FIGS. 9A-B show fluorescence microscopy results.
Figure 10A:
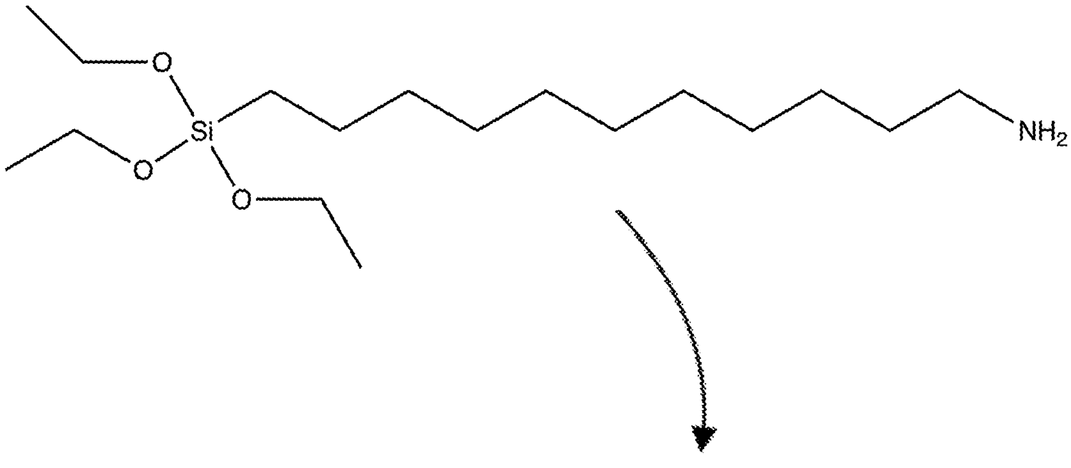
Figure 10A:
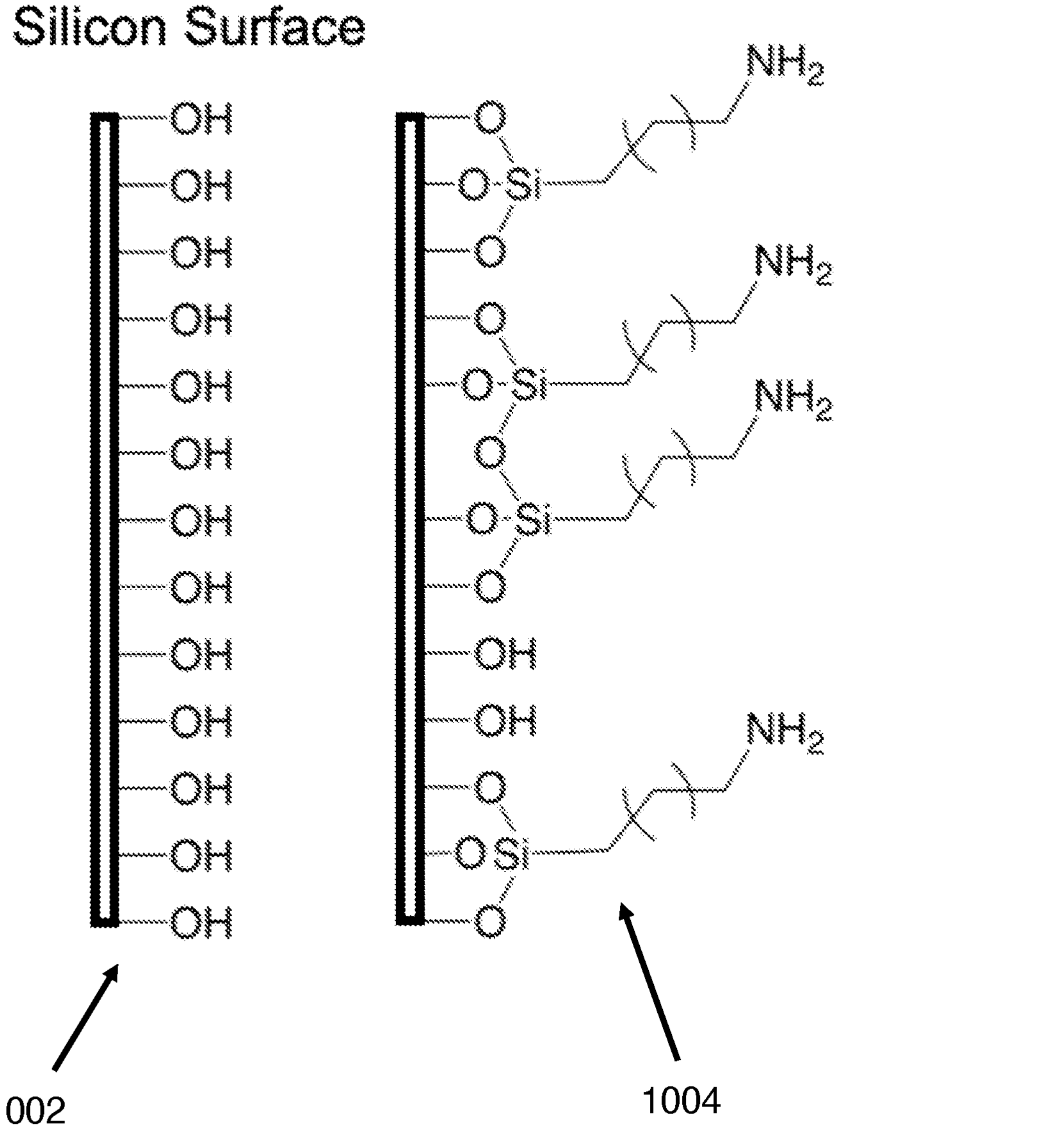
Figure 10C:
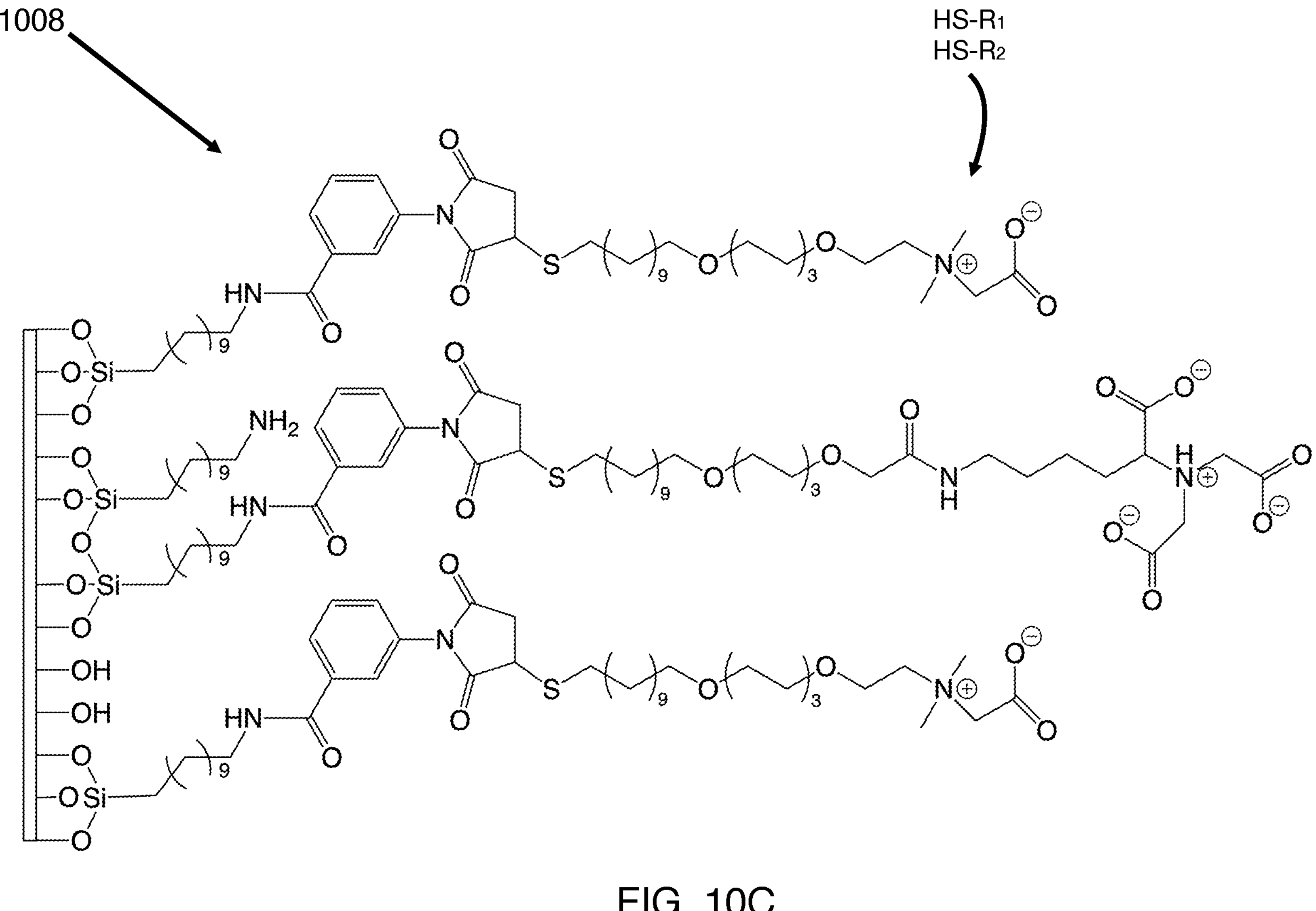
Figure 10D:
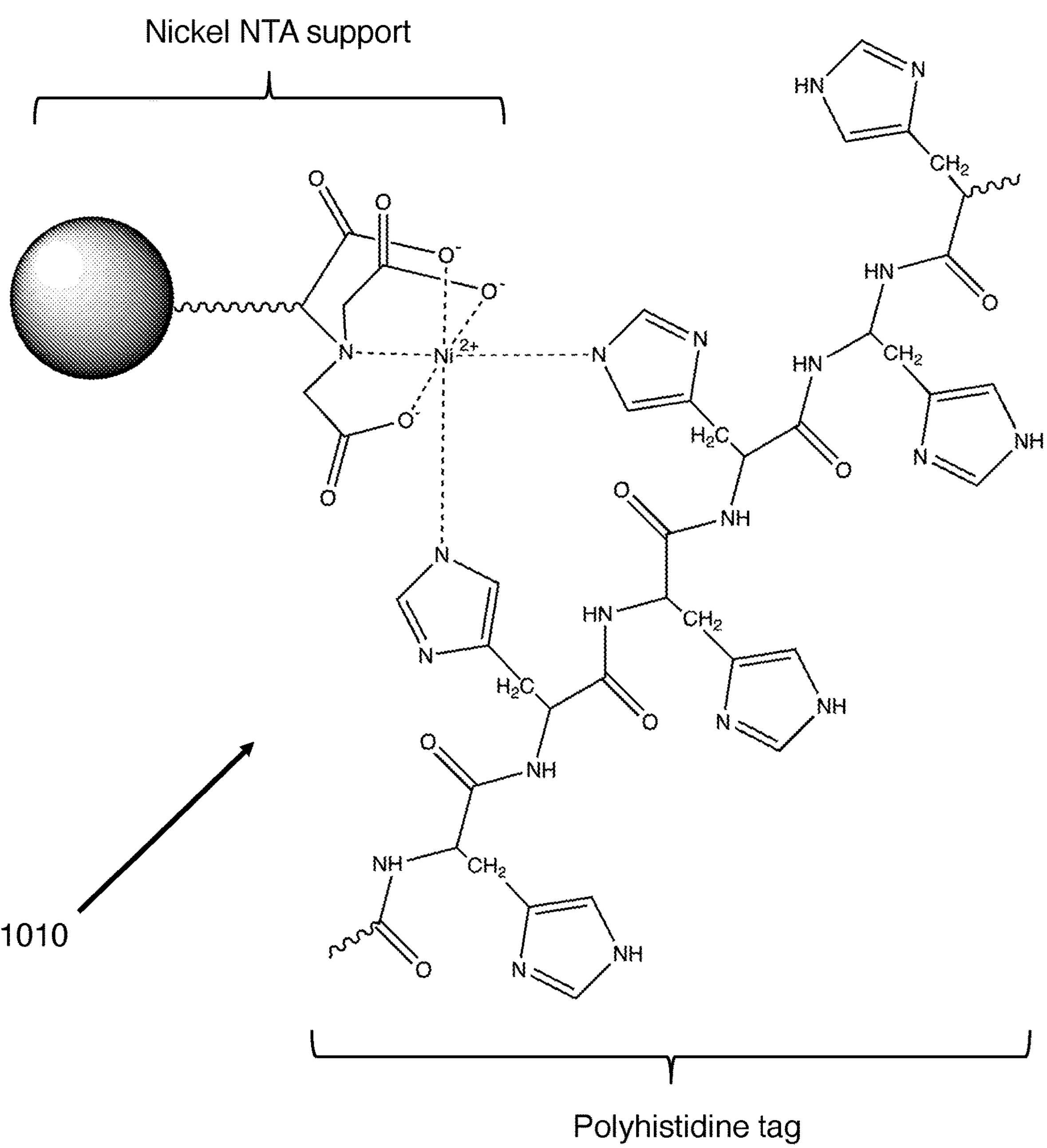
Figure 10E:
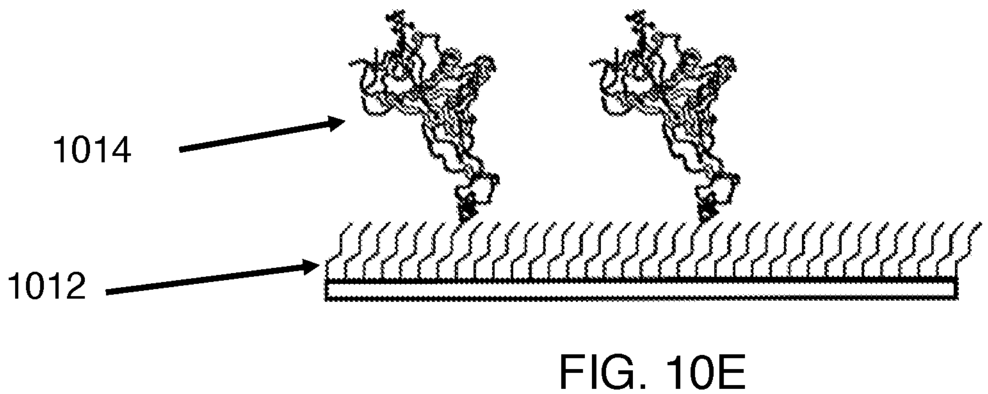
Figure 10F:
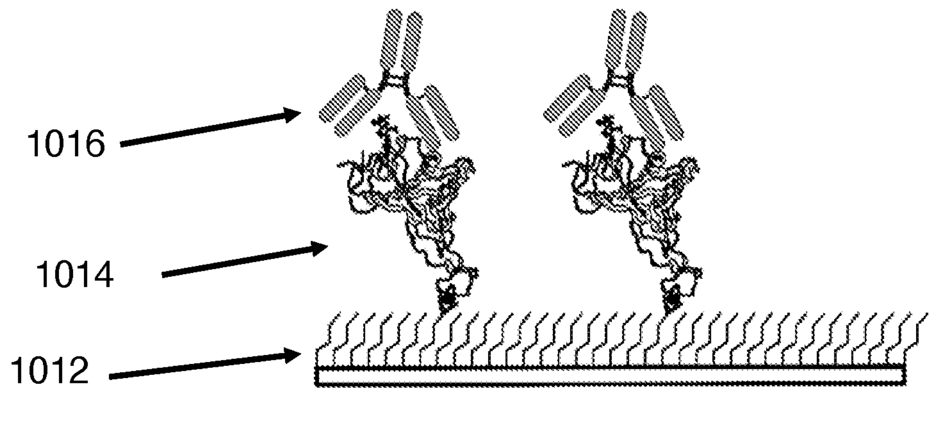

Pairing our resonators with specific probe DNA sequences offers specificity in target gene detection. To confirm specificity, we modify target DNA strands with ATTO590 fluorescent labels (FIG. 9A) and incubate sensors functionalized with probes that are only complementary to the nCoV.E sequence. Fluorescence imaging of sensors exposed to 10 μM solutions of target nCoV.E and HKU.ORF1 show significant binding only for the complementary E gene target and minimal signal for the noncomplementary ORF1 strands (FIG. 9B). This target specificity is also measured in the resonator scattering spectra, where resonance wavelength shifts are significant for complementary target-probe conditions and suppressed for non-specific binding (FIG. 5A). Our sensors exhibit concentration dependent responses from 1 μM to 10 nM (FIG. 5B). Measurements are taken for N=50-75 individual resonators at each target and concentration condition. The large variability in resonant wavelength shifts at each concentration are likely due to the stochastic nature of surface binding; notably, the signal from any particular resonator will depend on the local concentration and spatial position of bound targets (and hence binding at sites with the greatest electric field concentration will produce larger resonant shifts). Additionally, signal variation is also likely introduced through the hydrolytic degradation of silane layers in aqueous solutions during functionalization and hybridization experiments. We expect optimization of the surface functionalization homogeneity and stability to dramatically improve the performance of our sensors. Importantly, we are confident that this background signal, which is currently the dominant factor limiting our resolution, comes entirely from the instability of the sensing environment and not the photonic resonators themselves. We ultimately expect our detection threshold to be limited by the resonant linewidth, with shifts <0.1*FWHM easily measurable. We note that on our metasurface chips the silane linking chemistry will also non-specifically functionalize DNA probes to the surface oxide of the sapphire substrate. We estimate that only 0.0003% of surface bound target molecules contribute to the resonance shift of each resonator. Thus, our limit of detection could be reduced from 10 nM down to 10 fM with the introduction of microfluidic channels where only resonator regions are exposed to target molecules, utilization of a silicon specific surface functionalization process, or incorporation of additional nanostructures to isolate resonators from one another and increase sensor densities further. Additionally, the concentration dependent range of our device can potentially be tuned to different values of analyte concentration through modification of surface probe densities.

Two-way analysis of variance (ANOVA) and post-hoc Tukey's range test indicates that differences in scattered shift signals were statistically different for complementary vs. non-complementary targets at all tested concentrations (FIG.

5B inset). The increased measurement throughput and larger sample sizing of our platform can be used to significantly improve the accuracy of diagnostic studies, where multiple measurement redundancies allow for improved quantification and classification of sample populations. For example, we can classify "positive" complementary target detection against "negative" non-complementary target detection at each concentration based on thresholding resonant wavelength shift signals. Varying the threshold signal produces a receiver operating characteristic (ROC) curve, and the positive and negative signal discrimination is quantified as the area under the ROC curve (AUC). From this analysis, our sensors exhibit AUC values up to 0.98 (where AUC=1 indicates perfect signal discrimination and 0.5 represents no discrimination) and high sensitivity and specificity of 94 and 96% respectively. This increased digitization of target gene binding may also be paired with machine learning based analysis for further improved accuracy or to allow for discrimination of small signals due to genetic variants and point mutations.

Real-time measurement of resonators shows rapid target binding responses for a 100 nM solution of nCoV.E complementary targets measured across six representative resonators (FIG. 5C). Changes in the resonant wavelength greater than the measurement noise are detected within seconds and the binding signal plateaus within 5 minutes of sample introduction. The signal response shows excellent agreement with the Langmuir adsorption model (solid line FIG. 5C) with an observed hybridization rate constant of $7\times10^{-3}$ $s^{-1}$, comparable to other hybridization capture assays. These fast binding kinetics highlight a key advantage of chip-based approaches over conventional detection techniques that require time-intensive sequence amplification cycles.

B6) CONCLUSIONS

Our nanophotonic device offers a new platform for high throughput molecular analysis. We have demonstrated free space illuminated resonators with high-Q resonances in physiological media (2,200+) that can be patterned, tuned, and measured at densities exceeding 160,000 pixels per $cm^2$. Even larger Q's and greater feature densities are attainable in our platform with improved fabrication processes to reduce scattering losses from structural inhomogeneities, reduced absorption losses from biological media, and inclusion of photonic mirror elements to suppress light leakage as resonator chains are truncated below 50 μm. Interfaced with DNA probes, our metasurface design enables rapid, label-free, and highly digitized genetic screening that can bridge many of the challenges faced by conventional genetic analysis techniques. Paired with bioprinting procedures where different gene sequence probes are spotted across distinct sensing pixels, our high-Q metasurface chips can provide the foundation for rapid, label-free, and massively multiplexed photonic DNA microarrays. Furthermore, our nanophotonic chips are amenable to intensity imaging and/or hyperspectral imaging techniques that provide signal binding information without the need for a spectrometer, further reducing complexity and costs towards point of care genetic screening. Our platform promises unique possibilities for widely scaled and frequently administered genetic screening for the future of precision medicine, sustainable agriculture, and environmental resilience.

B7) SUPPLEMENTAL INFORMATION

B7.1) Spatial Distribution of Electric Fields Around Resonators

The sensitivity of a resonant mode to minute changes in the local refractive index can be estimated by the fraction of electric field energy residing outside the resonator. We calculate the exposure of the mode utilized in our sensors with the following equation:

$$f_{U_E} = \frac{\int_{V_{out}} \epsilon_{out}|E|^2 dV_{out}}{\int_{V_{in}} \epsilon_{in}|E|^2 dV_{in}}$$

where $\in_{0ut}$ and $\in_{in}$ are the permittivity of the medium containing the analyte and the permittivity of the resonator and substrate, respectively. $V_{0ut}$ and $V_{in}$ represent the volumetric regions of the analyte containing medium and the portions inside the resonator or substrate that do not overlap with any bound materials or molecules. Performing this analysis on the sensor design described above as well as guided mode resonant structures previously described in in the literature having notched silicon waveguides, we find that our silicon block chains significantly increase field penetration into the surrounding environment.

FIG. 6A shows electric field profile for notched silicon waveguide on a sapphire substrate. The upper panel shows an x-y cut through the center of the structure and the lower panel is an x-z cut through the center of the notch perturbation where fields are most strongly concentrated. FIG. 6B shows electric field profile for asymmetric chain of silicon blocks on a sapphire substrate. The upper panel shows an x-y cut through the center of the structure and the lower panel is an x-z cut through the center of the smaller block. Scale bar is 200 nm.

Field profiles of notched and block structures, respectively, are plotted in FIGS. 6A and 6B showing similar transverse electric waveguide modes. Due to the subwavelength spacing of the discrete silicon blocks in our sensors, we still excite the localized waveguide modes along the periodic direction that are seen in continuous silicon wire waveguides. However, the grating-like structure exposes regions of the mode to the surroundings while also reducing the effective mode index of the waveguide, leading to further extension of the fields out of the resonator. This design example results in the fraction of the mode energy in the surroundings to increase to $f_{uE}=0.29$ compared to only $f_{uE}=0.08$ for notched or continuous waveguide structures. It is convenient to refer to $f_{uE}$ as the free-space fraction of electric field energy.

B7.2) Quality Factor Scaling and Water Absorption

Figure 7:
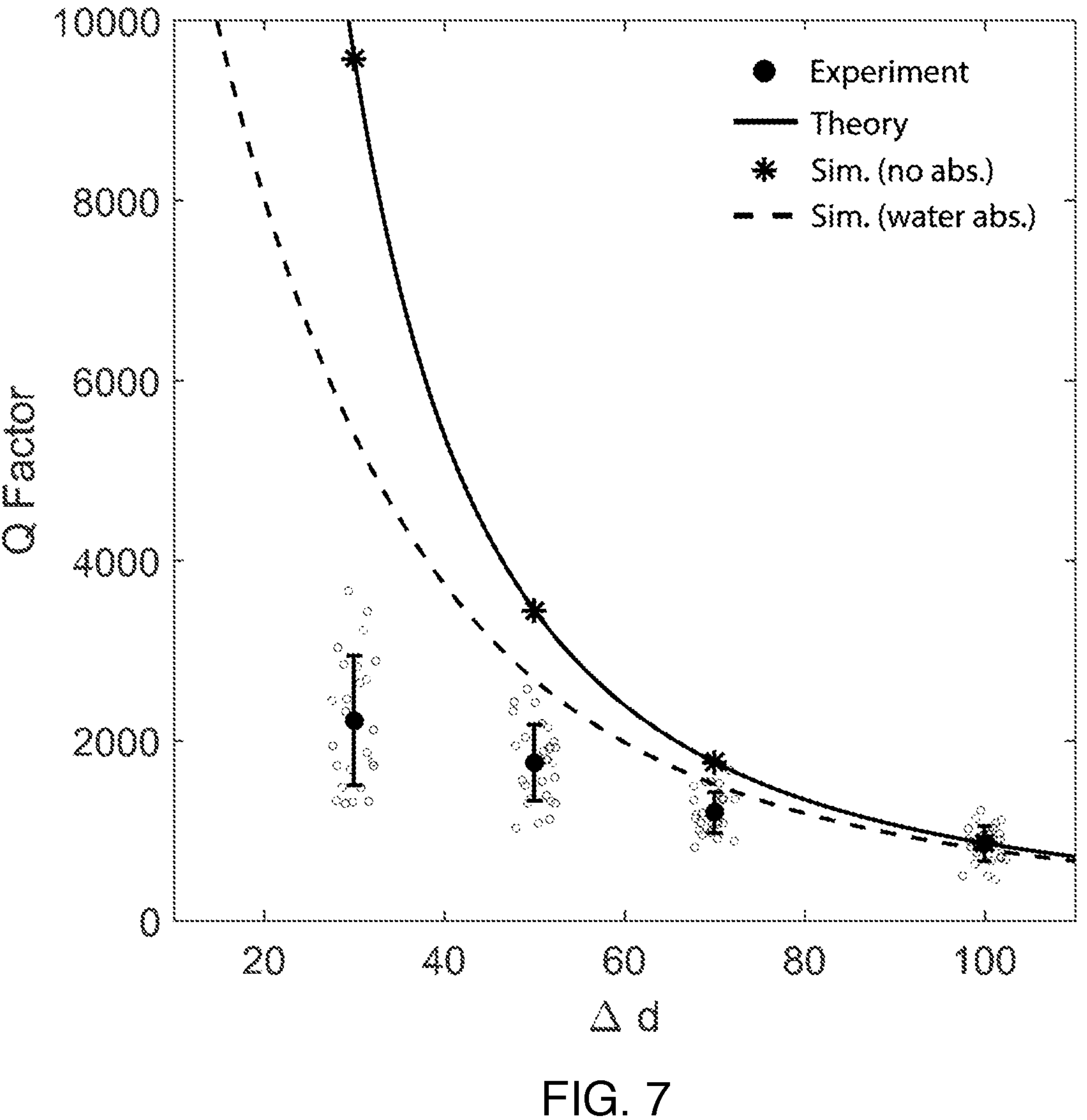
FIG. 7 shows the effect of perturbation depth on Q factor.

As discussed above, introducing an asymmetry along a silicon waveguide allows for the excitation of previously bound modes. Reduction of the asymmetry, Δd in the case of our metasurfaces, decreases the coupling strength of the mode to free-space radiation thereby increasing the Q factor. For a material that exhibits no intrinsic absorption losses, such as silicon in the near infrared, the Q factor can be arbitrarily increased as the perturbation strength approaches zero. This dependence of the Q factor on subtle structural deviations have been previously described through temporal coupled-mode theory and perturbation theory:

$$Q = \frac{B}{\alpha^2}$$

where B is a constant that depends on the resonator geometry and $\alpha$ is a unit-less asymmetry parameter represented by $\Delta d/d_0$ in our metasurface. This relationship is shown in FIG. 7, where theory (solid line) and numerical simulations (stars) indicate diverging Q factors as $\Delta d$ is decreased. We also observe that experimentally observed Q factors are lower than predicted values (experimental data from above text). One significant factor limiting our experimental quality factors is the absorption coefficient of water at telecommunication wavelengths. Since all our optical measurements are performed in aqueous solutions, dissipative losses are expected to decrease our measured Q factors as shown by the dashed line in FIG. 7, which represents numerical calculations including water absorption. The effects of absorption losses are particularly strong as $\Delta d$ is decreased, as longer resonance lifetimes lead to greater interaction between the resonant mode and the absorptive background medium. Future iterations of our sensor can be designed in the water absorption window around 1300 nm to maximize performance of the resonators. Additionally, fabrication imperfections such as surface roughness or non-uniformity in the metasurface structures will introduce scattering losses and reduce the observed Q factor.

B7.3) Finite Size Resonators

Figure 8A:
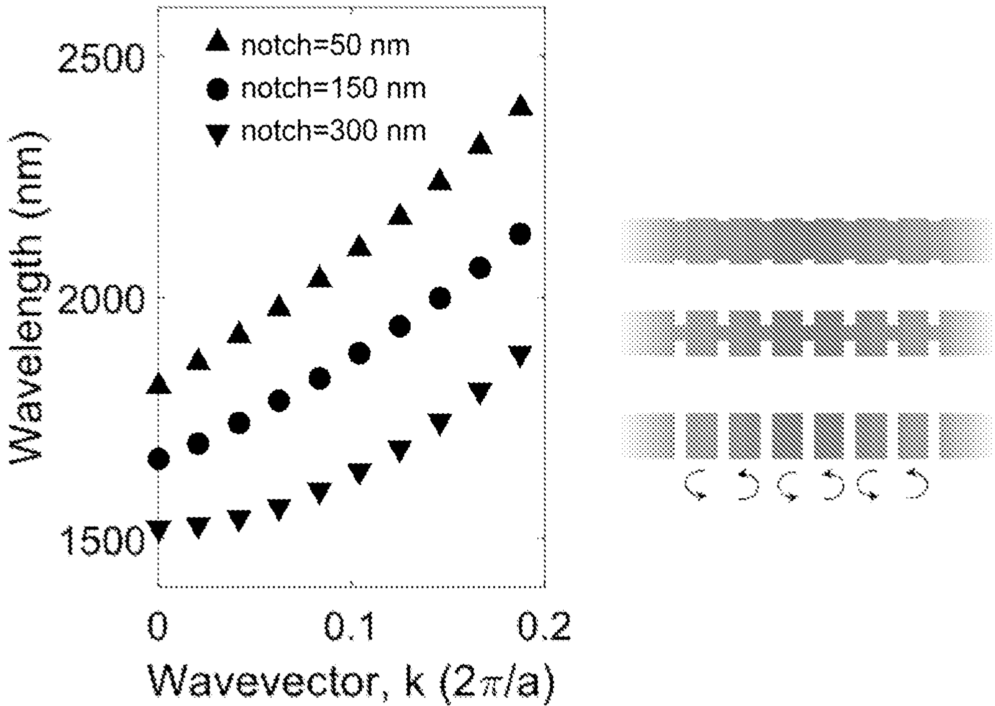
FIGS. 8A-D show the effect of waveguide length on resonator Q.
Figure 8B:
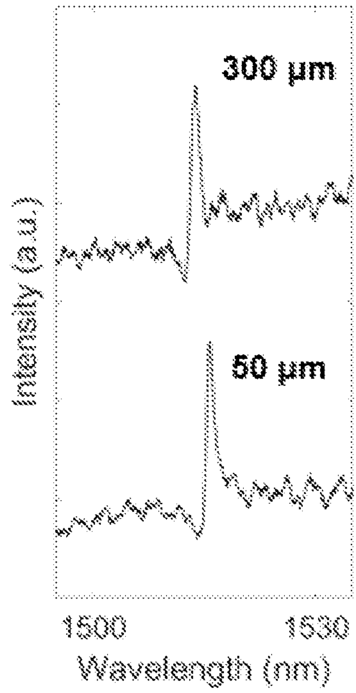
Figure 8C:
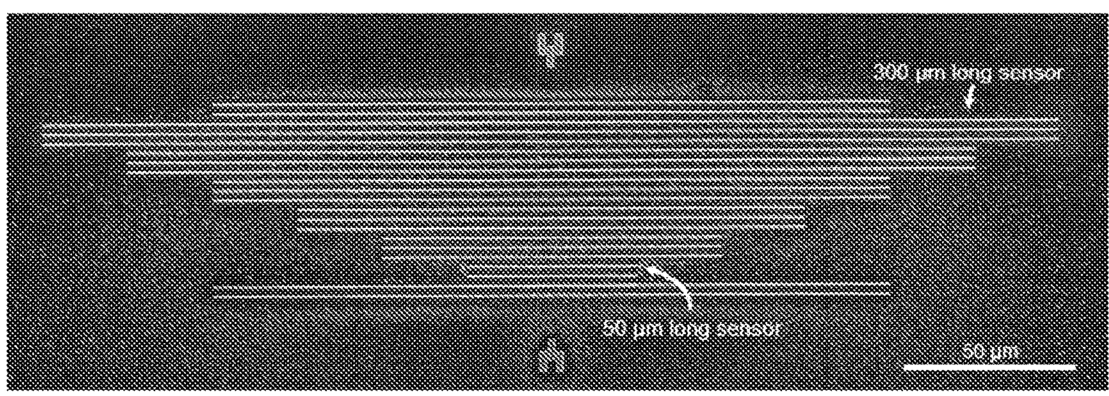
Figure 8D:
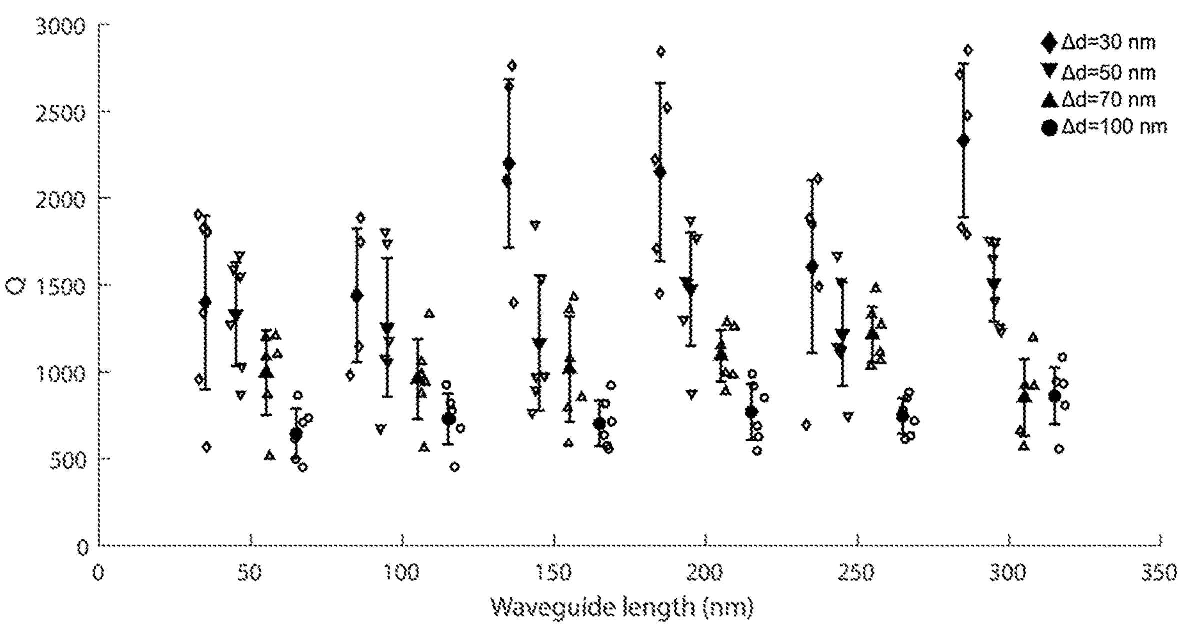

While the resonators shown above exhibit high-Q modes in longer 1-D arrays (200 μm), we show here that the resonators can be scaled down in length significantly while maintaining sharp spectral features. Our metasurface design features low scattering losses out the ends of the waveguides, and hence are relatively robust to resonator finite size effects due to the high index contrast between separated silicon blocks and gaps containing the background medium. In FIG. 8A, we show calculated dispersion diagrams for three different resonators having a solid silicon waveguide with increasing depths of notch corrugations (FIG. 8A, right). The waveguide has width of 600 nm and from top to bottom, the bands correspond to notches added on both sides of the waveguide with depths of 50, 150, and 300 nm. We observe flattening of the bands as the notch depth is increased to 300 nm, where the waveguide is now separated into distinct silicon blocks. The flatter bands indicate a much smaller group velocity due to strong in-plane Bragg scattering, which reduces the propagation of the mode out the waveguide ends and reduces effects of shrinking the resonator on the Q factor. We experimentally verify that we can maintain high quality factors while shortening the overall length of each resonator. In FIGS. 8B-C we show representative spectra (FIG. 8B) and SEM images (FIG. 8C) of multiple resonators with varying lengths from 300 μm down to 50 μm. Fitting N=6 resonators for each condition, FIG. 8D shows little change in the Q factor with varying waveguide length. Resonators with $\Delta d$=50 and 30 nm maintain high Q factors exceeding 1000 even in resonators down to 50 μm. Each resonator could potentially be further scaled down with added dielectric mirrors patterned on the waveguide ends to reduce scattering losses. Thus, it is possible to envision individual free space coupled high Q resonators with lengths on the order of a few μm.

B7.4) Fluorescence Microscopy

FIG. 9A shows a schematic of fluorescently tagged target DNA sequences. FIG. 9B shows fluorescence images and integrated intensities for sensors exposed to complementary nCoV.E sequences (top) and noncomplementary HKU.ORF1 sequences (bottom). Fluorescence imaging confirms the specificity of immobilized DNA probe molecules to complementary nucleic acid sequences. All metasurface sensors were functionalized with probes complementary only to the nCoV.E sequence.

Fluorescence experiments were performed after DNA hybridization experiments with target nucleic acids tagged with ATTO590 dye on the 5' end (FIG. 9A). Dried samples were placed in a Zeiss AxioImager system and imaged with a 20× objective. Fluorescence images were acquired with 1000 ms exposures on a Zeiss Axiocam 506 mono camera. Fluorescence intensity values were averaged over a 80×40 μm area and were normalized to the maximum intensity values from chips hybridized with complementary E gene targets (FIG. 9B).

B8) METHODS

B8.1) Computational Design

Electromagnetic simulations were performed with the Lumerical FDTD Solver. Metasurfaces were simulated with periodic boundary conditions in the x and y directions and perfectly matched layer (PML) boundary conditions in the z direction. Structures were excited with a plane wave polarized at 45° and injected from the negative z direction through a sapphire substrate. Transmission spectra were computed using a power monitor placed in the far field of the metasurface in the +z direction. Cross polarized transmission intensity was calculated as $$\text{Power})(-45°/(\text{Power}(-45°)+\text{Power}(+45°)).$$

B8.2) Fabrication

The metasurfaces were fabricated using standard lithographic procedures. First, 500 nm, single crystal silicon-on-sapphire (MTI Corp.) substrates were cleaned via sonication in acetone and isopropyl alcohol. The substrates were baked at 180° C. before spin coating with hydrogen silsesquioxane (HSQ) negative tone resist (XR-1541-06, Corning). The resist was baked for 40 min at 80° C. To reduce charging, a charge dissipation layer (e-spacer, Showa Denko) was spin coated over the HSQ resist and baked again for 5 min at 80° C. The metasurface patterns were defined by a 100 keV electron beam in a JEOL JBX-6300FS EBL system. Patterns were developed for 120 seconds in a 25% solution of tetramethylammonium hydroxide. Reactive ion etching with $Cl_2$, HBr, and $O_2$ chemistries were utilized to transfer the pattern to the silicon layer (Lam TCP 9400). The HSQ resist was removed using 2% hydrofluoric acid in water and the samples were then cleaned using a Piranha solution (9:1 $H_2SO_4$:$H_2O_2$) heated to 120° C. The silicon nanostructures were passivated by heating for 30 min at 800° C. in a furnace to grow a 4 nm oxide layer.

B8.3) Optical Characterization

Resonator spectra were measured in a home-built near-infrared microscope. Samples were illuminated via a broadband NKT supercontinuum laser with a collimated fiber output. A polarizer P1 was set to create linearly polarized incident illumination at a 45° angle with respect to the metasurface structures. The beam is weakly focused onto the sample through the sapphire substrate at normal incidence with a lens L2 (f=50 mm) to an approximate spot size of 200 μm. Additionally, all optical measurements in this work were taken with sample chips sealed in a fluid cell and immersed in PBS 1×. The scattered light is collected through a 50× objective lens (Olympus LCPLN50XIR) and directed through a cross-polarized polarizer P2 at 45° to reduce the substrate Fabry-Perot signal. The scattered light is then focused via a lens L3 (f=75 mm) into a SPR-2300 spectrometer (Princeton Instruments). The broadband signal is diffracted via a diffraction grating (600 g/mm, blaze wavelength 600 nm, Princeton Instruments) and focused onto an air-cooled InGaAs detector (NiRvana, Princeton Instruments). All spectral measurements are collected as the average of three successive 200 millisecond acquisitions. Spectral features were analyzed by fitting the data with the function:

$$T = \left| a_r + a_i i + \frac{b}{f - f_0 + \gamma i} \right|^2$$

where T is the scattered intensity from a superposition between a constant complex background, $a_r$+$a_i$i, and a Lorentzian oscillator with resonant frequency $f_0$ and full-width at half-maximum of 2γ. The quality factor is then calculated as $Q=f_0/2\gamma$.

B8.4) Surface Functionalization

Self-assembled monolayers of single stranded probe DNA was interfaced to the silicon metasurfaces through a multi-step chemical functionalization process. To activate the silicon surface for functionalization, the samples were immersed in a Piranha solution (9:1 $H_2SO_4$:$H_2O_2$) heated to 120° C. for 20 min to hydroxylate the surfaces. Next, samples were immersed in a 0.1 mM solution of 11-aminoundecyltriethoxysilane (Gelest Inc.) in ethanol, sealed, and left for overnight for 18-24 hrs. The samples were rinsed in fresh ethanol for 5 min (3×) and then baked for 1 hr at 150° C. to form a stable silane layer. A hetero-bifunctional cross linking molecule was attached to the silane layer through immersion in a 1 mM solution of 3-maleimidobenzoic acid N-hydroxysuccinimide ester (Millipore Sigma) dissolved in a 1:9 (v/v) mixture of dimethyl sulfoxide and PBS for 1 hr. Samples were then rinsed thoroughly with deionized water and blown dry with $N_2$ gas. Single stranded DNA probes were obtained from Integrated DNA Technologies (Coralville, IA) modified with a disulfide tether on the 3' ends. The as received DNA probes were dispersed in 50 μL of tris-EDTA buffer, pH 8.0, and mixed with 30 mg of DL-dithiothreitol for at least 1 hr to reduce the disulfide moieties to thiols. The probes were then purified via gravity-flow size exclusion chromatography using Illustra NAP-5 columns. The concentration of the eluted DNA solutions were determined using UV absorption signatures (Varian Cary 500 UV-Vis Spectrophotometer). For the functionalization reaction, portion of the stock solution were then diluted to 20 μM in PBS 1× with added divalent cations of 100 mM $MgCl_2$. The DNA probe solution was pipetted onto each sample and incubated overnight (~18-24 hrs) in a dark and humid environment. Samples were rinsed with PBS 1× and then soaked in a PBS solution with added salt to a concentration of 1M NaCl for 4 hours to remove any loosely bound or physiosorbed oligonucleotides. Samples were then rinsed with PBS 1× and deionized water and dried with $N_2$ gas. Samples corresponding to optical measurements in FIGS. 4B and 4D were measured before and after each functionalization step with additional deionized water rinsing and $N_2$ drying before the next chemical processing step. Samples corresponding to FIGS. 5A-C were optically characterized only before and after target DNA hybridization.

B8.5) DNA Hybridization

For static DNA hybridization measurements (all presented data in above excluding FIG. 5C), a baseline spectroscopic measurement was taken on metasurfaces that had been functionalized with a probe DNA monolayer. Probes with sequences corresponding to the E gene of the SARS-CoV-2 virus were used in all experiments. Following baseline measurements, samples were rinsed with DI water and dried. A target DNA solution corresponding to either complementary E gene or noncomplementary ORF1b gene fragments was produced by diluting a 100 μM stock solution to the desired concentration in 1× PBS. Additional divalent cations corresponding to 100 mM $MgCl_2$ were added to the solution to increase hybridization efficiency and speed. A 100 μL droplet of the target solution is then pipetted onto each sample chip and incubated for 30 min in a dark environment. Samples are rinsed in PBS 1× and deionized water before final optical characterization.

For dynamic DNA hybridization measurements presented in FIG. 5C, samples functionalized with DNA probes were placed in a fluid cell and mounted in the optical transmission set up described above. Spectral acquisitions were collected at 10 second intervals, and baseline measurements of the metasurfaces immersed in a pure hybridization solution with no nucleic acids are taken for 4 minutes. Next, excess volume of the target solution containing nucleic acids is flowed into the fluid cell from a syringe for 10 seconds via inlet tubing to displace the pure hybridization solution and completely fill the cell with target solution. Spectra are monitored for an additional 20 minutes and wavelength shifts are calculated based on changes compared to the average resonance wavelength obtained from the initial 4 minute baseline measurement.

C) Example 2—Protein Detection

The principles of the present invention can also be applied to protein detection, as in the following example.

Self-assembled monolayers (SAMs) of probe protein, RBD (receptor binding domain) region of the An2-SARS-CoV2 Spike protein, were bonded to the silicon metasurfaces through a five-step chemical functionalization process, summarized in FIGS. 10A-F. To activate the silicon surface for functionalization, the samples were immersed in a Piranha solution (9:1 $H_2SO_4$:$H_2O_2$) heated to 120° C. for 20 min to hydroxylate the surfaces (1002 on FIG. 10A). The chips were then baked for 10 min at 150° C. to ensure that no moisture is left on the chips. Next, the samples were immersed in a 0.1 mM solution of 11-aminoundecyltriethoxysilane (AUTES) (Gelest Inc.) in ethanol, sealed, and left for overnight for 18-24 hr at room temperature. The samples were then sonicated in fresh ethanol for 1 min and then rinsed with ethanol and deionized water for 1 min (3×). They were then baked for 1 hr at 150° C. to form a stable silane layer (1004 on FIG. 10A).

A hetero-bifunctional cross linking molecule was attached to the silane layer through immersion in a 1 mM solution of 3-maleimidobenzoic acid N-hydroxysuccinimide ester (MBS) (Millipore Sigma) dissolved in a 1:9 (v/v) mixture of dimethyl sulfoxide and PBS for 1 hr. Samples were then rinsed thoroughly with deionized water and blown dry with Argon gas (1006 on FIG. 10B).

The next building blocks for the SAM were purchased from Prochimia Surfaces (Gdynia, Poland). At this step, two bioresistant, zwitterionic, thiolated ligands were functionalized on the surface at varying ratios to achieve a desired protein surface density for the final SAM. A first molecule terminates with a Carboxybetaine end group (ZI 003), (HS-C11-(EG)4-Carboxybetaine), used as a non-binding background molecule, and a second molecule terminates with nitrilotriacetic acid (TH 007), (HS-C11-(EG)3-NTA), necessary for subsequent probe protein attachment. For the functionalization of our surfaces, the ZI 003 sample was dissolved in ethanol to form a liquid stock solution at a concentration of 10 mM, while TH 007 was dissolved in deionized water to form a liquid stock solution at 10 mM. These solutions were then diluted to a final concentration of 1 mM and mixed in varying ratios in order to vary the protein probe density on the surface. The samples were immersed in 2 mL of this 1 mM solution of varying ratios of ZI 003 and TH 007, sealed, in a dark environment, and left overnight for 12 hours at room temperature. Samples were then rinsed with deionized water for 30 seconds and subsequently soaked in a 1× PBS solution for 1 hr to remove any loosely bound or physiobsorbed thiolated molecules. They were then rinsed again with deionized water for 60 seconds and dried with Argon gas (1008 on FIG. 10C).

Samples were then incubated with a Ni(II) Chloride solution made from anhydrous Nickel(II) chloride powder dissolved in deionized water to a final concentration of 5 g/L in order to chelate the Ni ions with the nitrilotriacetic acid (NTA), to form a Ni(II)-NTA complex for forming a strong bond with our probe protein. For this step, the samples were immersed in 2 mL of Ni(II) solution, sealed, and left for 2 hours at room temperature (1010 on FIG. 10D).

Samples were then rinsed with deionized water for 30 sec and dried with Argon gas. Finally, the SAM was terminated with the functionalization of our probe protein, the RBD region of the SARS CoV-2 Spike protein, produced in the lab of Professor Scott Boyd at Stanford University, and subsequently modified with the addition of a polyhistidine tag formed of 6 histidine amino acids at the c-terminus of the protein. Stock protein solution was diluted to a final concentration of 2 ug/mL in 1× PBS. Samples were covered with 2 mL of stock solution, sealed, and let to incubate for 1 hour at room temperature. Samples were then rinsed thoroughly with 1×PBS to remove any unbound or loosely bound proteins. See FIG. 10E. Here 1014 is the probe protein and 1012 is the SAM.

Finally, samples were incubated with our target antibodies, Recombinant An2-SARS-CoV-2 Spike Glycoprotein S1 antibodies, CR3022, purchased from Abcam (Cambridge, UK). The antibody solution was diluted in 1× PBS to a final concentration of 5 ug/mL. Samples were then incurred in 1 mL of solution, sealed, and left to incubate at room temperature for 1 hr. Samples were subsequently rinsed thoroughly with 1× PBS, and final sample measurements were collected. See FIG. 10F. Here 1016 is the target antibodies, 1014 is the probe protein and 1012 is the SAM.

Figure 11A:
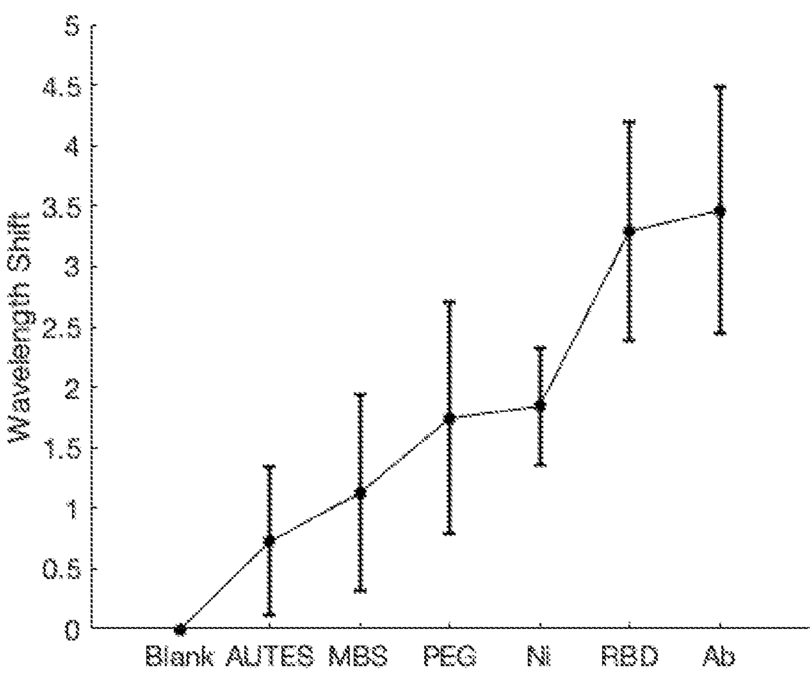
FIGS. 11A-B show resonant wavelength shifts due to the surface functionalization of FIGS. 10A-F, and due to binding of a target protein.
Figure 11B:
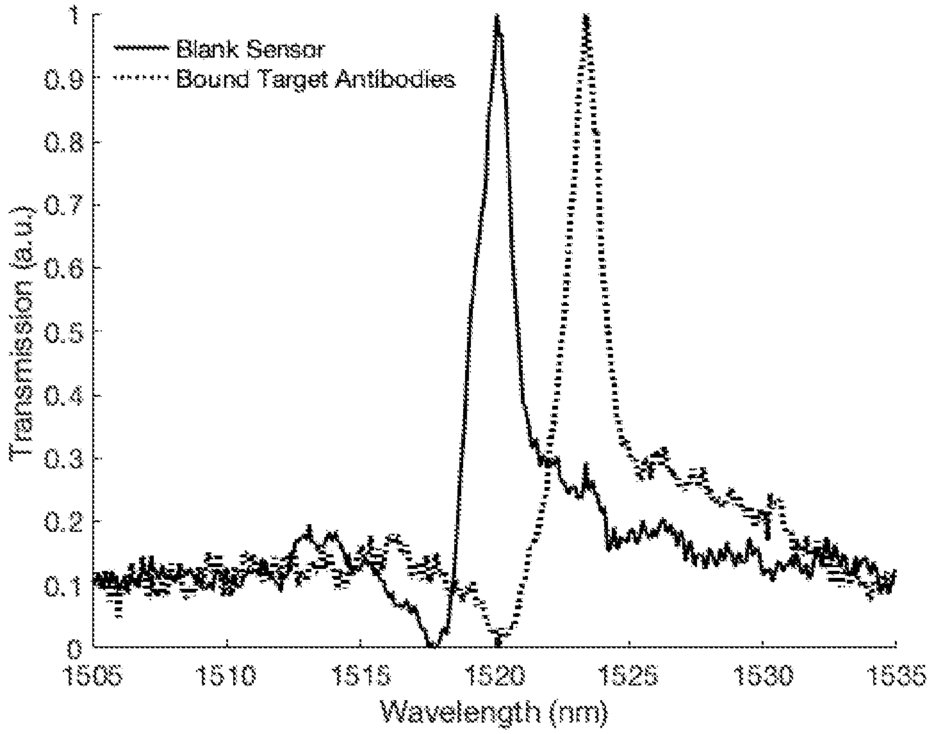

Samples corresponding to the optical measurements taken in FIGS. 11A-B were measured before and after each functionalization step. All measurements were taken while the chip was immersed in 1× PBS. For all steps other than those with proteins present (protein probe and target antibody samples), chips were rinsed with deionized water and dried with Argon gas after measurements were taken and before subsequent incubation steps. After incubation with probe protein molecules, samples remained immersed in 1× PBS and were rinsed in 1× PBS to avoid sample drying and protein denaturation.

FIG. 11A shows the measured spectral shifts after each functionalization step. This plot shows clear resonant wavelength shifts as consecutive molecular monolayers of AUTES, MBS, thiolated PEG-NTA, Ni(II), probe protein, and the antibody sample are layered onto the resonator surface.

FIG. 11B shows the final shift between the silicon chip and the final antibody sample, with data collected from N=15 resonators.

The invention claimed is:

1. An apparatus comprising: an electromagnetic metasurface, surface functionalized for selective molecular binding of one or more molecules or analytes in proximity to the electromagnetic metasurface, including one or more waveguides disposed on a substrate; wherein each of the one or more waveguides is to support one or more guided mode resonances and has a corresponding longitudinal perturbation, and a selected one or more of the guided mode resonances is to couple free-space radiation by the corresponding longitudinal perturbation; and the selected one or more guided mode resonances, in operation, have electric field distributions that extend outside the electromagnetic metasurface.

2. The apparatus of claim 1, further comprising an optical source configured to provide the free-space radiation, wherein the electric field distributions, that extend outside the electromagnetic metasurface, are associated with resonant wavelength shifts based on the surface functionalization and on the selective molecular binding of one or more molecules or analytes to the electromagnetic metasurface.

3. The apparatus of claim 1, further comprising an optical detector configured to receive output radiation from the electromagnetic metasurface, wherein the output radiation is selected from the group consisting of: reflected radiation, transmitted radiation, scattered radiation, diffracted radiation, and Raman-scattered radiation.

4. The apparatus of claim 3, wherein the optical detector is configured to determine a spectrum of the output radiation based on dispersion caused by the one or more waveguides, wherein the electric field distributions, that extend outside the electromagnetic metasurface, are associated with resonant wavelength shifts based on the surface functionalization and on the selective molecular binding of one or more molecules or analytes.

5. The apparatus of claim 1, further comprising the surface functionalization disposed on the electromagnetic metasurface to selectively bind one or more analytes in proximity to the electromagnetic metasurface.

6. The apparatus of claim 5, wherein the one or more analytes are selected from the group consisting of: nucleic acids, proteins, small molecules, extracellular vesicles, pathogens and whole cells.

7. The apparatus of claim 5, wherein a detection sensitivity of the one or more analytes is 10 fM (femtomolar) or better, whereby detection of the one or more analytes without a prior analyte amplification step is provided.

8. The apparatus of claim 5, wherein a dynamic range for detection of the one or more analytes is 10 dB (decibels) or more.

9. The apparatus of claim 1, wherein the electromagnetic metasurface is configured as an array of one or more sensor pixels, each sensor pixel including a corresponding part or all of one of the one or more waveguides.

10. The apparatus of claim 9, wherein the array of one or more sensor pixels is selected from the group consisting of 1-dimensional arrays and 2-dimensional arrays.

11. The apparatus of claim 9, further comprising per-pixel selective surface functionalization, whereby multiplexed sensing of two or more distinct analytes is provided.

12. The apparatus of claim 1, wherein the selected one or more guided mode resonances have a free-space fraction of electric field energy of 0.2 or more.

13. The apparatus of claim 1, wherein resonance wavelength shifts are enhanced in response to one or more complementary target-probe conditions and suppressed for non-specific binding, and the electric field distributions, that extend outside the electromagnetic metasurface, are associated with resonant wavelength shifts based on the surface functionalization and on the selective molecular binding of one or more molecules or analytes.

14. The apparatus of claim 1, further including an optical detector to respond to resonance wavelength shifts being enhanced due to one or more complementary target-probe conditions.

15. The apparatus of claim 1, further including an optical detector to respond to resonance wavelength shifts being enhanced, relative to a baseline reference, due to one or more complementary target-probe conditions.

16. The apparatus of claim 1, further including an optical detector to provide environmental sensing in response to the selected one or more guided mode resonances having electric field distributions that extend outside the electromagnetic metasurface, and to resonance wavelength shifts being enhanced due to one or more complementary target-probe conditions.

17. The apparatus of claim 1, wherein the one or more waveguides are disposed on the substrate to mitigate light scattering losses out ends of the waveguides, light is to be transmitted or reflected as incident light from the electromagnetic metasurface, and the electromagnetic metasurface includes subwavelength nanoantennas to confine light in a near field region, which is proximal the subwavelength nanoantennas, and to control light scattering in a region distal to the subwavelength nanoantennas.

18. The apparatus of claim 1, wherein the one or more waveguides include or correspond to distinct and separated dielectric blocks.

19. The apparatus of claim 1, wherein the one or more waveguides include separated blocks, each including dielectric material, wherein sets of immediately adjacent ones of the separated blocks are spaced by respective gaps to facilitate exposure of the electric field energy into a medium surrounding the electromagnetic metasurface.

20. A method comprising: using a functionalized electromagnetic metasurface, including one or more waveguides disposed on a substrate, to selectively molecular bind one or more molecules or analytes in proximity to the electromagnetic metasurface, wherein each of the one or more waveguides supports one or more guided mode resonances and has a corresponding longitudinal perturbation; and causing a selected one or more of the guided mode resonances to couple free-space radiation by the corresponding longitudinal perturbation and the selected one or more guided mode resonances to have electric field distributions that extend outside the electromagnetic metasurface.

* * * * *